(12) United States Patent
Burgeson et al.

(10) Patent No.: US 6,689,936 B1
(45) Date of Patent: Feb. 10, 2004

(54) METHOD FOR EVALUATING A COMPOUND FOR ITS EFFECT ON SKIN

(75) Inventors: Robert Burgeson, Marbleland, MA (US); Satoshi Amano, Komae (JP); Jiro Kishimoto, Wellesley, MA (US); Toshio Nishiyama, Tokyo (JP); Ritsuko Ehama, Yokohama (JP)

(73) Assignee: The General Hospital Corp., Boston, MA (US)

( * ) Notice: Subject to any disclaimer, the term of this patent is extended or adjusted under 35 U.S.C. 154(b) by 0 days.

(21) Appl. No.: 09/393,483

(22) Filed: Sep. 10, 1999

Related U.S. Application Data

(63) Continuation-in-part of application No. 09/070,436, filed on Apr. 30, 1998.
(60) Provisional application No. 60/069,945, filed on Dec. 17, 1997.

(51) Int. Cl.$^7$ ................................................ A01K 67/00
(52) U.S. Cl. ............................................. 800/3; 800/18
(58) Field of Search .................................. 800/3, 8, 18

(56) References Cited

FOREIGN PATENT DOCUMENTS

| EP | 0 633 315 | 1/1995 |
|---|---|---|
| WO | WO 96 37237 | 11/1996 |

OTHER PUBLICATIONS

Cachon–Gonzalez PNAS, USA, vol. 91, pp. 7717–7721, 1994.*
Mohan J. Investigative Dermatology, vol. 106, p. 906, abstract 605, 1996.*
Davis Dev. Biol., vol. 170, pp. 726–729, 1995.*
Mullins J. Clin. Invest., vol. 98, pp. S37–S40, 1996.*
Simkiss "Transgenic birds," Animals with novel genes, Maclean, N., ed., Cambridge University Press, pp. 106–137, 1994.*
Overbeek "Factors affecting transgenic animal production," Transgenic animal technology, pp. 96–98, 1994.*
Braghetta J. Cell Biol., vol. 135, pp. 1163–1177, 1996.*
Mullins et al., Expression of the DBA/2J ren–2 gene in the adrenal gland of transgemic mice, 1989, The EMBO Journal, vol. 8, pp. 4065,4072.*
Mullins et al., Fulminant hypertension in transgenic rats harbouring the mouse ren–2 gene, 1990, Nature, vol. 344, pp. 541–544.*
Hammer et al., Spontaneous inflammatory disease in transgemic rats expressing HLA–B27 and Human B2m: An animal model of HLA–B27–associtaed human disorders, 1990, Cell, vol. 63, pp. 1099–1112.*
Taurog et al., HLA–B27 in inbred and non–inbred transgenic mice: Cell surface expression and recognition as an alloantigen in the absence of human B2–microglobulin, 1988, The Journal of Immunology, vol. 141, pp. 4020–4023.*

Okabe et al., Grenn mice as a source of ubiquitous green cells, 1997, FERS Letters, vol. 407, pp. 313–319.*
Kishimoto et al., Developmental study of human versican promoter–lacz fusion gene in trangenic mice, 1997,37th Annual meeting of the American Society for Cell Biology, Washington, D.C., Dec. 13–17, vol. 8.*
Kishimoto et al., Human version promoter–driven lacz activity in transgenic mouse skin and hair dermal papilla, 1998, 3rd Joint meeting of the European Society for Dermatological Research, Japanese Society for Investigative Dermatology Cologne, Germany.*
Braghetta et al., "Distinct Regions Control Transcriptional Activation of the α1 (VI) Collagen Promoter in Different Tissues of Transgenic Mice", *The Journal of Cell Biology*, vol. 135, No. 4, pp. 1163–1177 (1996).
Cachon–Gonzalez et al. "Structure and Expression of the Hairless Gene of Mice", Proc. Natl. Acad. Sci., USA, vol. 91, pp. 7717–7721 (1994).
Gille Jens et al: "Transforming growth factor—alpha—induced transcriptional activation of the vascular permeability factor (VPF/FEGF) gene requires AP–2–dependent DNA binding and transactivation." EMBO (European Molecular Biology Organization) Journal, vol. 16, No. 4, 1997, pp. 750–759, XP002164519.
Ramirez, A. et al.: "A 5'–upstream region of a bovine keratin 6 gene confers tissue–specific expression and hyperproliferation–related induction in transgenic mice." Proceedings of the National Academy of Sciences of the United States of America, vol. 92, May 1995, pp. 4783–4787, XP002156382.
Bernstein, E.F. et al.: "evaluation of sunscreens with various sun protection factors in a new transgenic mouse model of cutaneous photoaging that measure elastin promoter activation" Journal of the American Academy of Dermatology, US, C.V. Mosby, St. Louis, MO, vol. 37 , No. 5, Part 01, Nov. 1997, pp. 725–729, XP002117296.
Ikawa, M. et al.: "Green fluorescent proten as a marker in transgenic mice" Development of growth and differentiation, JP, Japanese Society of Developmental Biologists, vol. 37, Aug. 1, 1995, pp. 455–459, XP002086829.
Damak et al. *"Expression of Human Neutrophil Elastase Gene in the Lungs of Transgenic Mice"*, J. Cellular & Biochemistry Supp., Abstract V102; Apr. 3, 1992.
Himelstein et al., Oncogene 14(16): 1995–1998 (1997).
Kemp et al. "The Glycosylation of Alpha–1 Antitrypsin in Transgenic Mice", *Animal Cell Technology: Basic: Applied Aspects, 8th Annual Conference*, edited by Funatsu et al., the Netherlands: Kluwer Academic Publishers 8:517–522 (1997).
Rice et al., Bone, 21(6):479–486 (Dec. 1997).
Simon et al. *J. of Biological Chemistry*, 272(16):10651–10663 (Apr. 18, 1997).

(List continued on next page.)

*Primary Examiner*—Michael Wilson
(74) *Attorney, Agent, or Firm*—Fish & Richardson PC

(57) ABSTRACT

The invention provides methods of evaluating a treatment for its effect on skin. The invention also provides non-human transgenic animals, e.g., mice, having a reporter gene coupled to a skin-metabolism promoter.

14 Claims, 8 Drawing Sheets

OTHER PUBLICATIONS

Yoshizaki et al. *Cancer*, 79(1):139–144.
Mohan et al., *J. Investigative Dermatology*, 106:906, Abstract 604 (1996).
Davis et al., *Develop. Biol.*, 170:726–729 (1995).
Chalfie et al., *Science*, 263:802–804 (1994).
Zhang et al., *Biochem. Biophys. Res. Commun.*, 227:707–711 (1996).
Mistelli & Spector, *Nat. Biotechnol.*, 15:961–964 (1997).
Chiocchetti et al. *Biochem. Biophys. Act.*, 1352:193–202 (1997).
Okabe et al. *FEBS letters*, 407:313–319 (1997).
Zhuo et al. *Dev. Biology*, 187:36–42 (1997).
Detmar et al., *J. Invest. Dermatol.*, 106:207–208 (1996).
Brown, et al. *J. Exp. Med.*, 176:1375–1379 (1992).
Larcher et al. *Cancer Res.*, 56:5391–5396 (1996).
Begona et al. *Proc. Natl. Acad. Sci.*, 91:7717–7721 (1994).
Bernstein et al., *Laboratory Investigation*, 72:662–669 (1995).
Huhtala et al., *The Journal of Biological Chemistry*, 266:16485–16490 (1991).
Itano et al., *Biochemical and Biophysical Research Communications*, 222:816–820 (1996).
Mauch et al., *Arch. Dermatol. Res.*, 287:107–114 (1994).
Naso et al., *The Journal of Biological Chemistry*, 269:32999–33008 (1994).
Spicer et al. *The Journal of Bioligical Chemistry*, 272:8957–8961 (1997).
Takahashi et al. *The Journal of Biological Chemistry*, 263:14739–14747 (1988).
Tischer et al. *The Journal of Biological Chemistry*, 266:11947–11954 (1991).
Watanabe et al. *The Journal of Biological Chemistry*, 271:22945–22948 (1996).
Hsu–Wong et al. *The Journal of Biological Chemistry*, 269:18072–18075 (1994).
Bernstein et al. *Photochemistry and Photobiology*, 64:369–374 (1996).

* cited by examiner

Human Versican-LacZ Transgene Construction

hMHr4 N3S (BgII/XhoI)/p.VAS5-NE (η3836p)

```
         10         20         30         40         50         60         70         80         90
GAATTCgcct gggtgaaagt gagttcccg ttggaggcaa cagacgagga gaggatgaa ggcctggccc ccaagaatga gccctgaggt
CTTAAGcgga cccactttca ctcaaggggc aacctccgtt gtctgctcct ctcctacctt ccggaccggg ggttcttact cgggactcca 100        110   PstI   120        130        140        150        160        170        180
tcagggagcg gctggagtga gccggccccaˌGATCTcccga ggtcctgaag gaagagagta aagccatgtc tgctgttttc tagaggctgc
agtccctcgc cgacctgcact cggccggggt CTAGAgggct ccaggacttc ctttctctat ttcggtacag acgacaaaag atctccgacg 190        200        210        220        230        240        250        260        270
tactgtcccc tttactgccc tgaagattca gcctgcggaa gacaggggt tgccccagtg gaattcccca gccttgccta gcagagccca
atgacagggg aaatgacggg acttctaagt cggacgcctt ctgtcccca acggggtcac cttaagggggt cggaacggat cgtctgggt 280        290        300        310        320        330        340        350        360
ttccttccgc ccccagatga agcagggaga ggaagctgag tcaaagaagg ctgtcaggga gggaaaaaga ggacagagcc tggagtgtgg
aaggaaggcg ggggtctact tcgtcccctct ccttcgactc agtttcttcc gacagtccct ccctttttct cctgtctcgg acctcacacc 370        380        390        400        410        420        430        440        450
ggaggggctt ggggaggata tctgacctgg gaggggtgt tgcaaaaggc caaggatggg ccaggggggat cattagtttc agaaagaagt
cctccccaaa cccctcctat agactgacc ctcccccaca acgttttccg gttcctaccc ggtcccccta gtaatcaaag tcttttcttca 460        470        480        490        500        510        520        530        540
ctcagggagt ctttccatcac tttcccttgg ctgaccactg gaggctttca gaccaaggga tgggggatcc ctccagcttc atccccctcc
gagtccctca gaaggtagtg aaagggaacc gactggtgac ctccgaaagt ctggttccct accccctagg gaggtcgaag taggggagg 550        560        570        580        590        600        610        620        630
ctccctttca tacagttccc acaagctctg cagtttgcaa aaccctaccc ctccctgag ggcctgcggt ttcctgcggg tctggggtct
gagggaaagt atgtcaaggg tgttcgagac gtcaaacgtt ctgggatggg gaggggactc ccggacgcca aaggacgccc agaccccaga 640        650        660        670        680        690        700        710        720
tgcctgacttt ggcagtggag actgcgggca gtggagagag gaggagtgg tgtaagccct ttctcatgct ggtgctgcca cacacacaca
acggactgaa ccgtcacctc tgacgcccgt cacctctctc ctcctccacc acattcggga aagagtacga ccacgacggt gtgtgtgtgt 730        740        750        760        770        780        790        800        810
cacacacaca cacacacaca cacacacaca ccctgacccc tgagtcagca ctgcctgctc aaggaggggt gggtcacag gagcgcctcc
gtgtgtgtgt gtgtgtgtgt gtgtgtgtgt gggactgggg actcagtcgt gaacgggacag ttcctcccca ccccagtgtc ctcgcggagg 820        830        840        850        860        870        880        890        900
ttaaagcccc cacaacagca gctgcagtca gacacctctg ccctcacccT CGAGaactg aaaaaccaga aagttaactg gtaagtttag
aatttcgggg gtgttgtcgt cgacgtcagt ctgtggagac gggagtggGA GCTCcttgac ttttgtgtct ttcaattgac cattcaaatc
                                                    XhoI 910        920        930        940        950        960        970        980        990
tcttttttgtc ttttattcca ggtcccggat ccggtgtgg tgcaaatcaa agaactgctc ctcagtggat gttgccttta cttctaggcc
agaaaaacag aaaataaagt ccagggccta ggccaccacc acgtttagtt tcttgacgag gagtcacctca caacgaaat gaagatccgg 1000       1010       1020       1030       1040       1050       1060       1070       1080
tgtacggaag tgttacttct gctctaaaag ctgcggaatt gtacccgcgg ccgcaattcc cgggatcga aagacctgc taaagcaaaa
acatgccttc acaatgaaga cgagattttc gacgccttaa catgggggcc ggcgttaagg gcccctagct ttctcggacg atttcgttt 1090       1100       1110       1120       1130       1140       1150       1160       1170
aagaagtcac catgtcgttt actttgacca acaagaacgt gatttttcgtt gccggtctgg gaggcattgg tctgacacc agcaaggagc
ttcttcagtg gtacagcaaa tgaaactggt tgttcttgca ctaaaagcaa cggccagacc ctccgtaacc agacctgtgg tcgttcctcg 1180       1190       1200       1210       1220       1230       1240       1250       1260
tgctcaagcg cgatcccgtc gtttacaac gtcgtgactg ggaaaaccct ggcgttaccc aacttaatcg ccttgcagca catcccctt
acgagttcgc gctagggcag caaaatgttg cagcactgac ccttttggga ccgcaatggg ttgaattagc ggaacgtcgt gtagggggaa 1270       1280       1290       1300       1310       1320       1330       1340       1350
tcgccagctg gcgtaaatgc gaagaggccc gcaccgatcg cccttcccaa cagttgcgca gcctgaatgg cgaatgcggc tttgctggt
agcgtcgac cgcattatcg ctctccggg cgtgctagc gggaaggttt gtcaacgcgt cggacttacc gcttaccgcg aaacggacca 1360       1370       1380       1390       1400       1410       1420       1430       1440
ttccggcacc agaagcggtg ccggaaagct ggctggagtg cgatcttcct gaggcgata ctgtcgtcgt ccctcaaac tggcagatgc
aaggccgtgg tcttcgccac ggccttttcga ccgacctcac gctagaagga ctccggctat gacagcagca ggggagtttg accgtctacg 1450       1460       1470       1480       1490       1500       1510       1520       1530
acgttacga tgcgcccatc tacaccaacg taacctatcc cattacggtc aatccgccgt ttgttcccac ggagaatccg acgggttgtt
tgccaatgct acgcgggtac atgtggttgc attggatagg gtaatgccag ttaggcggca aacaagggtg cctcttaggc tgcccaacaa 1540       1550       1560       1570       1580       1590       1600       1610       1620
actcgctcac atttaatgtt gatgaaagct ggctacagga aggccaagcg cgaattattt ttgatggcgt taactcggcg tttcatctgt
tgagcgagtg taaattacaa ctactttcga ccgacntcct tccggtctgc gcttaataaa aactaccgca attgagccgc aaagtagaca 1630       1640       1650       1660       1670       1680       1690       1700       1710
ggtgcaacgg gcgctgggtc ggttacggcc aggacagtcg tttgccgtct gaatttgacc tgagcgcatt tttacgcgcg ggagaaaacc
ccacgttgcc cgcgacccag ccaatgccgg tcctgtcagc aaacggcaga cttaactgg actcgcgtaa aaatgcgcgc cctcttttgg 1720       1730       1740       1750       1760       1770       1780       1790       1800
gcctcgcggt gatggtgctg cgttggagtg acggcagtta tctgaagat caggatatgt ggcggatgag cggcattttc cgtgacgtct
cggagcgcca ctaccacgac gcaacctcac tgccgtcaat agacttcta gtcctataca ccgcctactc gccgtaaaag gcactgcaga 1810       1820       1830       1840       1850       1860       1870       1880       1890
cgttgctgca taaaccgact acacaaatca gcgatttcca tgttgccact cgctttaatg atgtttcag ccgcgctgta ctgagcctg
gcaacgacgt atttggctga tgtgtttagt cgctaaaggt acgaaattac taaaaagtc ggcgcgacat gactctccgac 1900       1910       1920       1930       1940       1950       1960       1970       1980
aagttcgat gtgcggcgag ttgcgtgact acctacgggt aacagttttct ttatggcagg gtgaaacgca ggtcgccagc ggcaccgcgc
ttcaagtcta cacgccgctc aacgactga tggatgccca ttgtcaaaga aatacctcc cactttgcgt ccagcggtcg ccgtggcgcg 1990       2000       2010       2020       2030       2040       2050       2060       2070
ctttcggcgg tgaaattatc gatgagcgtg tgtgttatgc cgatcgcgtc acactacgtc tgaacgtcga aaaccgaaa ctgtggagcg
gaaagccgcc actttaatag ctactcgcac caccaatacg gctagcgcag tgtgatgcag acttgcagct tttgggcttt gacctcgc 2080       2090       2100       2110       2120       2130       2140       2150       2160
ccgaaatccc gaatctctat cgtgcggtgg ttgaactgca caccgccgac ggcacgctga ttgaagcaga agcctggcgt gtcggtttcc
ggctttaggg cttagagata gcacgccacc aacttgacgt gtggcggctg ccgtgcgact aacttcgtct tggacgcta cagccaaagg 2170       2180       2190       2200       2210       2220       2230       2240       2250
gcgaggtgcg gattgaaaat ggtctgctgc tgctgaacgg caagcgttg ctgattcgag gcgttaaccg tcacgagcat catctctgc
cgctccacgc ctaacttttta ccagacgacg acgacttgcc gttcgggaac gactaagctc cgcaattggc agtgctcgta gtaggagacg 2260       2270       2280       2290       2300       2310       2320       2330       2340
atggtcaggt catggatgag cagacgatgg tgcaggatat cctgctgatg aagcagaaca actttaaccg cgtgcgctgt tcgcattatc
taccagtcca gtacctactc gtctgctacc acgtcctata ggacgactac ttcgtcttgt tgaaattcgg gcacgcgaca agcgtaatag 2350       2360       2370       2380       2390       2400       2410       2420       2430
cgaaccatcc gctgctggtac acgctgtgcg accgctacgg cctgtatgtg gtggatgaag ccaatattga aacccagtgg atggtgccaa
gcttggtagg cgacaccatg tgcgacacgc tggcgatgcc ggacatacac cacctacttc ggttataact ttgggtgcgg taccacggtt
```

```
         7300       7310       7320       7330       7340       7350       7360       7370       7380
    cgccagctgg cgaaagggggg atgtgctgca agggattaa gttgggtaac gccagggttt tcccagtcac gacgttgtaa aacgacggcc
    gcggtcgacc gcttttcccc tacacgacgt tcccctaatt caacccattg cggtcccaaa agggtcagtg ctgcaacatt ttgctgccgg
         7390       7400       7410       7420       7430       7440       7450       7460       7470
    a,t
    t,a
```

FIGURE 4 (cont'd)

METHOD FOR EVALUATING A COMPOUND FOR ITS EFFECT ON SKIN

This application is a continuation-in-part of U.S. Ser. No. 09/070,436, filed Apr. 30, 1998., which claims benefit from the previously filed Provisional Application No. 60/069,945 filed Dec. 17, 1997, which are hereby incorporated by reference.

BACKGROUND OF THE INVENTION

The invention relates to transgenic animals which express reporter genes coupled to promoters of genes involved in the health, aging, or appearance of the skin, e.g., theversican, VEGF, or MMP promoters, and methods of using such animals in evaluating treatments, e.g., compounds, for their effect on skin.

SUMMARY OF THE INVENTION

The inventors have discovered that transgenic animals having one or more constructs which include a skin-metabolism promoter coupled to a reporter gene can be used to evaluate a treatment, e.g., the removal of hair, e.g., by plucking or shaving, or the administration of a compound, for use in enhancing the health or appearance of the skin.

Accordingly, the invention features, a method of evaluating a treatment, e.g., the removal of hair, e.g., by plucking or shaving, or the administration of a compound, for its effect on skin. The method includes:

providing a transgenic animal having a reporter gene coupled to a skin metabolism-related promoter, preferably a human promoter;

administering the treatment to the transgenic animal or a tissue therefrom; and evaluating expression of the reporter gene, thereby evaluating the treatment for its effect on skin.

The treatment, e.g., the administration of a compound, can be administered to a live animal. In other embodiments, the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or transgenic mammal.

In preferred embodiments evaluating includes detection of a signal, e.g., a fluorescent signal, with a confocal microscope. In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, see Takeda et al., 1991, *L. Am. Geriatr.* 39:911–919, or a transgenic mutant mouse which exhibits a phenotype of accelerated aging. The most preferred animals are mice.

In preferred embodiments, the promoter is heterologous from the transgenic animal, i.e., the promoter is from another species. In other preferred embodiments the promoter is from the same species as the transgenic animal. In particularly preferred embodiments, the skin metabolism-related promoter is a human skin metabolism-related promoter. In particularly preferred embodiments, the skin metabolism-related promoter is: a promoter from a gene which encodes a transmembrane protein or a component of the extracellular matrix, such as a proteoglycan promoter, e.g., a versican promoter; a promoter from a protease expressed in the skin, e.g., a matrix metalloproteinase (MMP) promoter, e.g., an MMP1, MMP2, MMP3, MMP4, MMP5, MMP6, MMP7, MMP8, or MMP9 promoter; a promoter from a gene which affects vascular function, e.g., a vascular endothelial growth factor promoter; a hyaluronan synthase promoter, e.g., a hyaluronan synthase 1 promoter, a hyaluronan synthase 2 promoter, or a hyaluronan synthase 3 promoter; a promoter for a collagenase expressed in the skin, e.g., a MMP2 or MMP9, preferably a MMP9, promoter; or a neutrophil elastase promoter.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the transgenic animal further includes a second reporter gene coupled to a second skin metabolism-related promoter, wherein the second skin metabolism-related promoter is different from the first skin metabolism-related promoter. The reporter gene coupled to the first promoter can be the same or different from the reporter gene coupled to the second promoter. For example, the transgenic animal can include: a first reporter gene coupled to the versican promoter and a second reporter gene coupled to the vascular endothelial growth factor promoter; a first reporter gene coupled to the versican promoter and a second reporter gene coupled to a hyaluronan synthase promoter; a first reporter gene coupled to the hyaluronan synthase promoter and a second reporter gene coupled to the vascular endothelial growth factor promoter; a first reporter gene coupled to a matrix metalloproteinase (MMP) promoter and a second reporter gene coupled to a MMP2 or MMP9, preferably MMP9, promoter; a first reporter gene coupled to a matrix metalloproteinase (MMP) promoter and a second reporter gene coupled to the neutrophil elastase promoter; or a first reporter gene coupled to a MMP2 or MMP9, preferably a MMP9, promoter and a second reporter gene coupled to the neutrophil elastase promoter. In preferred embodiments, the transgenic animal can include two constructs both of which are upregulated. In preferred embodiments, the transgenic animal can include two constructs both of which are downregulated.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment) to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound for its effect on skin. The method includes:

providing a transgenic animal, e.g., a mouse, having a reporter gene coupled to a, preferably human, versican promoter;

administering a treatment, e.g., the removal of hair, e.g., by plucking or shaving, or the administration of a compound, to the transgenic animal, or to a tissue taken therefrom; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the versican promoter is a human versican promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment) to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound, for its effect on skin. The method includes:

providing a transgenic animal, e.g., a mouse, having a reporter gene coupled to a, preferably human, matrix metalloproteinase promoter;

administering the treatment to the transgenic animal, or to a tissue taken therefrom; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the matrix metalloproteinase promoter is a human matrix metalloproteinase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound, for its effect on skin. The method includes:

providing a transgenic animal, e.g. a mouse, having a reporter gene coupled to a vascular endothelial growth factor promoter;

administering the treatment to the transgenic animal; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the vascular endothelial growth factor promoter is a human vascular endothelial growth factor promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound, for its effect on skin. The method includes:

providing a transgenic animal, e.g., a mouse, having a reporter gene coupled to a, preferably human, hyaluronan synthase promoter;

administering the treatment to the transgenic animal; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the hyaluronan synthase promoter is a human hyaluronan synthase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound, for its effect on skin. The method includes:

providing a transgenic animal, e.g., a mouse, having a reporter gene coupled to, a preferably human, MMP2 or MMP9, preferably a MMP9, promoter;

administering the treatment to the transgenic animal, or to a tissue taken therefrom; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, a MMP2 or MMP9, preferably a MMP9, promoter is a human MMP2 or MMP9, preferably a MMP9, promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a second treatment to the transgenic animal. The second treatment can be one which injures or damages the skin, kills skin cells, or can include the removal of hair, e.g., by plucking, shaving, or application of a depilatory, or in general, induces an unwanted condition of the skin. The second treatment can be the application of water, a drying agent, an irritant, an inflammatory agent, light or UV irradiation. Reporter gene expression in response to the treatment can be determined in the presence of the second treatment, and optionally compared to the response seen in the absence of the second treatment.

In another aspect, the invention features, a method of evaluating a treatment, e.g., the removal of hair, e.g., by plucking or shaving, or the administration of a compound, for its effect on skin. The method includes:

providing a transgenic animal, e.g., a mouse, having a reporter gene coupled to a, preferably human, neutrophil elastase promoter;

administering the treatment to the transgenic animal, or to a tissue taken therefrom; and evaluating expression of the reporter gene, thereby evaluating the treatment for its effect on skin aging.

The treatment, e.g., the administration of a compound, can be administered to a live animal. In other embodiments the treatment, e.g., the administration of a compound, is administered to a tissue, e.g., a cell, taken from a transgenic animal.

The effect of the treatment, e.g., the administration of a compound, can be evaluated in a living transgenic animal, a dead transgenic animal, or tissue taken from either a living or dead transgenic animal.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In preferred embodiments, the treatment includes the administration of a compound and the compound is administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the neutrophil elastase promoter is a human neutrophil elastase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In preferred embodiments, the treatment is administered repeatedly, preferably prior to evaluation of reporter gene evaluation.

In preferred embodiments, the treatment includes the administration of a compound and the method further includes one or more subsequent administrations of the compound to the transgenic animal. In preferred embodiments, the compound is administered to the transgenic animal for a period of at least one, two, three, or four weeks. The compound can be administered at a constant level or at a range of different levels. In preferred embodiments, the compound is administered to the transgenic animal before, during, or after UV irradiation or other skin damaging treatment.

In preferred embodiments, the method further includes comparing the expression of the reporter gene to a control value, e.g., the level of expression of the reported gene in an untreated transgenic animal.

In preferred embodiments, the method further includes evaluating the expression of the reporter gene coupled to the second skin metabolism-related promoter.

In preferred embodiments, the compound is: a cosmetic; a non-toxic substance; a substance approved for human drug or cosmetic use in one or more jurisdictions; a retinoid or derivative thereof; TGFβ; of TGFα.

In preferred embodiments, the method further includes administering a treatment (other than the compound) to the transgenic animal. The treatment can be one which injures or damages the skin, kills skin cells, or in general, induces an unwanted condition of the skin. The treatment can be the application of water, a drying agent, an irritant, an inflammatory agent, light or UV irradiation. Reporter gene expression in response to the compound can be determined in the presence of the treatment, and optionally compared to the response seen in the absence of the treatment.

In another aspect, the invention features, a non-human transgenic animal described herein, e.g., a transgenic animal having a reporter gene coupled to a versican promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, see Takeda et al., 1991, *L. Am. Geriatr.* 39:911–919, or a transgenic mutant mouse which exhibits a phenotype of accelerated aging. The most preferred animals are mice.

In particularly preferred embodiments, the versican promoter is a human versican promoter.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features, a non-human transgenic animal, e.g., a mouse, or a tissue taken therefrom, having a reporter gene coupled to a matrix metalloproteinase promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the matrix metalloproteinase promoter is a human matrix metalloproteinase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features, a non-human transgenic animal, e.g., a mouse, or a tissue taken therefrom, having a reporter gene coupled to a vascular endothelial growth factor promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the vascular endothelial growth factor promoter is a human vascular endothelial growth factor promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features, a non-human transgenic animal, e.g., a mouse, or a tissue taken therefrom, having a reporter gene coupled to a hyaluronan synthase promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the hyaluronan synthase promoter is a human hyaluronan synthase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features, a non-human transgenic animal, e.g., a mouse, or a tissue taken therefrom, having a reporter gene coupled to a Type IV collagenase promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, a MMP2 or MMP9, preferably a MMP9, promoter is a human a MMP2 or MMP9, preferably a MMP9, promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features, a non-human transgenic animal, e.g., a mouse, or a tissue taken therefrom, having a reporter gene coupled to a neutrophil elastase promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In particularly preferred embodiments, the neutrophil elastase promoter is a human neutrophil elastase promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter gene encodes a product which can be detected with relative ease, e.g., an enzyme, e.g., an enzyme which produces a colored or luminescent product. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene.

In another aspect, the invention features a promoter-reporter gene construct described herein.

In another aspect, the invention features a method of analyzing GFP presence or distribution in a tissue. The method includes:

providing a tissue sample, e.g., a tissue section, which includes GFP;

evaluating or detecting fluorescent emission, or the lack of fluorescent emission, wherein said detecting step is performed prior to washing or fixing with an aqueous solution, thereby analyzing GFP in a tissue.

In preferred embodiments the tissue is frozen prior to the detection step. The sample is not contacted with a fixing agent prior to detection.

In preferred embodiments: the tissue is from a transgenic animal, e.g., a transgenic mini-pig, guinea pig, rat or mouse, e.g., a hairless or nude mouse, a senescence accelerated mouse, e.g., SAM mice, see Takeda et al., 1991, *L. Am. Geriatr.* 39:911–919, or a transgenic mutant mouse which exhibits a phenotype of accelerated aging; the GFP is expressed from a transgenic sequence encoding GFP or under the control of a transgenic control element, e.g., a transgenic promoter or enhancer.

In preferred embodiments the promoter is a human promoter.

In preferred embodiments detection includes examination of the sample with a microscope, e.g., a fluorescent or epi-fluorescent microscope.

In preferred embodiments evaluating includes detection of a signal, e.g., a fluorescent signal, with a confocal microscope.

Animals described herein can be used in this method.

In another aspect, the invention features, a method of determining the stage of the hair cycle in an animal which expresses a reporter molecule in hair follicle, e.g., the outer root sheath of the hair follicle. The method includes evaluating or detecting the presence or absence of reporter expression, presence being associated with a growing hair cycle (anagen) and absence with a resting hair cycle (telegen and catogen).

In preferred embodiments the reporter molecule is under the control of a promoter expressed in the hair follicle, e.g., the outer root sheath.

In preferred embodiments the promoter is a human promoter.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter molecule is GFP.

In preferred embodiments the animal is a transgenic animal, e.g., a transgenic mini-pig, guinea pig, rat or mouse, e.g., a hairless or nude mouse, a senescence accelerated mouse, e.g., SAM mice, or a transgenic mutant mouse which exhibits a phenotype of accelerated aging;

Animals described herein can be used in this method.

In preferred embodiments the promoter is a VEGF promoter, a versican promoter, or other promoter described herein.

In another aspect, the invention features, a method of analyzing wound healing. The method includes: providing an animal which expresses a reporter molecule under the control of a VEGF promoter, detecting the presence or absence of reporter molecule in a wound, thereby analyzing wound healing.

In preferred embodiments the detection step is reported.

In preferred embodiments, the animal, tissue from the animal, is subjected to a treatment, e.g., the administration of a compound. In such embodiments the method can be used to evaluate the effect of the treatment on wound healing. It may be desirable to compare results from a treated subject or tissue with an untreated subject or tissue.

In a preferred embodiment the reporter is a luminescent or fluorescent product, which preferably, can lumenesce or fluoresce without the addition of exogenous substrates or cofactors, e.g., green fluorescent protein.

In preferred embodiments the reporter molecule is GFP.

In preferred embodiments the animal is a transgenic animal, e.g., a transgenic mini-pig, guinea pig, rat or mouse, e.g., a hairless or nude mouse, a senescence accelerated mouse, e.g., SAM mice, or a transgenic mutant mouse which exhibits a phenotype of accelerated aging.

Animals described herein can be used in this method.

In preferred embodiments the promoter is a human promoter.

In another aspect, the invention features, a method of analyzing GFP expression in a transgenic animal having a GFP transgene. The method includes:

a first step of evaluating or detecting the presence or absence of GFP in the animal or in a tissue from the animal; and (optionally)

a second step of evaluating or detecting the presence or absence of GFP in the animal or in a tissue from the animal; and thereby analyzing GFP expression.

In preferred embodiments (in this method and in other methods disclosed herein) the GFP is red shifted GFP.

In preferred embodiments the animal is a transgenic animal, e.g., a transgenic mini-pig, guinea pig, rat or mouse, e.g., a hairless or nude mouse, a senescence accelerated mouse, e.g., SAM mice, or a transgenic mutant mouse which exhibits a phenotype of accelerated aging. An animal described herein can be used in this method.

In preferred embodiments at least 1, 5, 10, 20, 30, or 60, 180, 365 days elapse between first and second step.

In preferred embodiments the tissue is skin tissue.

In preferred embodiments the detection steps are performed on a live animal.

In preferred embodiments the promoter is a human promoter.

In preferred embodiments evaluating includes detection of a signal, e.g., a fluorescent signal, with a confocal microscope.

In another aspect, the invention features, a method of analyzing the expression of a transgene on a transgenic animal, e.g., a transgenic mouse or pig. The method includes:

providing a live transgenic animal;

evaluating or detecting the presence or absence of a reporter gene, e.g., GFP, encoded by a transgenic sequence or under the control of a transgenic control element, e.g., a promoter or enhancer;

thereby analyzing the expression of a transgene.

In preferred embodiments the animal is a transgenic animal, e.g., a transgenic mini-pig, guinea pig, rat or mouse, e.g., a hairless or nude mouse, a senescence accelerated mouse, e.g., SAM mice, or a transgenic mutant mouse which exhibits a phenotype of accelerated aging. Animals described herein can be used in the methods.

In preferred embodiments the reporter is under the control of a VEGF promoter or another promoter described herein.

In preferred embodiments the promoter is a human promoter.

In preferred embodiments the promoter is one which is expressed on the skin.

In preferred embodiments evaluating includes detection of a signal, e.g., a fluorescent signal, with a confocal microscope.

In preferred embodiments the tissue is skin tissue.

In preferred embodiments the detection steps are performed on a live animal.

In preferred embodiments the method is repeated at least once during the life of the animal. The first and a subsequent repetition of the method can be separated by as much as 1, 10, 30, 60, 90, 180, 365, or 700 days.

In a preferred embodiment the reporter is a luminescent or fluorescent product, which preferably, can lumenesce or fluoresce without the addition of exogenous substrates or cofactors, e.g., green fluorescent protein.

In another aspect, the invention features, a method of evaluating gene expression in a live animal. The method includes:

providing a live transgenic animal having a transgene which includes a reporter gene, e.g., GFP, e.g., red shifted GFP;

evaluating or detecting the presence or absence of reporter molecule, e.g., GFP, in the live transgenic animal, thereby evaluating gene expression in the live animal.

In preferred embodiments, the sequence which encodes a reporter gene is under the control of a preselected promoter, e.g., a human promoter. The preselected promoter can be, a skin metabolism-related promoter, e.g.,: a promoter from a gene which encodes a transmembrane protein or a component of the extracellular matrix, such as a proteoglycan promoter, e.g., a versican promoter; a promoter from a protease expressed in the skin, e.g., a matrix metalloproteinase (MMP) promoter, e.g., an MMP1, MMP2, MMP3, MMP4, MMP5, MMP6, MMP7, MMP8, or MMP9 promoter; a promoter from a gene which affects vascular function, e.g., a vascular endothelial growth factor promoter; a hyaluronan synthase promoter, e.g., a hyaluronan synthase 1 promoter, a hyaluronan synthase 2 promoter, or a hyaluronan synthase 3 promoter; a promoter for a collagenase expressed in the skin, e.g., a MMP2 or MMP9, preferably a MMP9, promoter; or a neutrophil elastase promoter.

The VEGF promoter is a preferred promoter. In preferred embodiments the promoter is one which is up or down regulated in inflammatory angiogenesis, or neoplastic growth.

In preferred embodiments, the animal is a non-human transgenic animal. For example, the transgenic animal can be a transgenic mini-pig, a transgenic guinea-pig, a transgenic rat, or a transgenic mouse, e.g., a hairless mouse, a nude mouse, a senescence accelerated mouse, e.g., SAM mice, or a transgenic mutant mouse which exhibits a phenotype of accelerated aging. The most preferred animals are mice.

In preferred embodiments, a treatment is administered to the animal any of before, during, or after valuation of reporter gene expression. The treatment can be the administration of a compound. The compound can be administered by: applying the compound to the skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments evaluating includes detection of a signal, e.g., a fluorescent signal, with a confocal microscope.

In preferred embodiments evaluating includes detection of a signal, e.g., a fluorescent signal, with a confocal microscope.

In preferred embodiments the evaluation of the expression of the reporter gene step is repeated at least once during the life of the animal. The first and a subsequent repetition of the step can be separated by as much as 1, 10, 30, 60, 90, 180, 365, or 700 days. Both the first and a subsequent repetition can be performed on a live animal, e.g., with the use of a confocal microscope.

In a preferred embodiment the reporter is a luminescent or fluorescent product, which preferably, can lumenesce or fluoresce without the addition of exogenous substrates or cofactors, e.g., green fluorescent protein.

Methods of the invention can be performed in vivo, with whole animals, or in vitro, that is, with tissue, e.g., skin, or cells, which are derived from a transgenic animal described herein or with cells, preferably skin cells or tissue, from cells transformed with a skin-metabolism promoter/reporter gene construct.

As used herein, a "transgenic animal" is an animal, e.g., a non-human mammal, e.g., a mini-pig, a guinea-pig, or a rodent, e.g., a mouse or a rat, in which one or more, and preferably essentially all, of the cells of the animal include a transgene. The transgene can be introduced into the cell, directly or indirectly by introduction into a precursor of the cell, e.g., by microinjection, transfection or infection, e.g., by infection with a recombinant virus. The term genetic manipulation is directed to the introduction of a recombinant DNA molecule. This molecule may be integrated within a chromosome, or it may be extrachromosomally replicating DNA.

Transgenic animals can be, e.g., heterozygous or homozygous for a transgene.

As used herein, the term "rodent" refers to all members of the phylogenetic order Rodentia.

As used herein, the term "reporter gene" refers to a nucleic acid sequence which is fused downstream of a skin metabolism-related promoter, such that its expression is under the control of the promoter. Reporter genes usually encode a protein whose activity can be easily measured. For example, the reporter gene can be a gene encoding an assayable protein, e.g., an enzyme, not found in the cell in nature, e.g., a beta-galactosidase gene, a luciferase gene, a green fluorescent protein gene, an alkaline phosphatase gene, a horseradish peroxidase gene, a chloramphenicol acetyl transferase gene, luciferase, and the like. In a preferred embodiment the reporter product is capable of providing a signal which indicates the activity of the promoter to which it is linked. Preferred reporters are those which luminesce or fluoresce. Preferred reporters can luminesce or fluoresce, in vivo, without the addition of an exogenous substrate. A particularly suitable reporter is green fluorescent protein. Modified variants of green fluorescent protein, e.g., EGFP, EBFP, EYFP, d2EGFP, ECFP, GFPuv are included within the term green fluorescent protein. EGFP is particularly preferred. These variants of GFP are commercially available by C1ONTECH, Laboratories, Inc. Palo Alto, Calif. Furthermore, GFP and variants thereof, are provided in the following references, all of which are incorporated by referenced: Chalfie, M. et al. (1994) Science 263:802–805; Prasher, D. C., et al. (1992) Gene 111:229–233; Inouye, S. & Tsuji, F. I. (1994) FEBS Letters 341:277–280; Wang, S. & Hazelrigg, T. (1994) Nature 369:400–403; Cody, C. W., et al. (1993) Biochemistry 32:1212–1218; Inouye, S. & Tsuji, F. I. (1994) FEBS Letters 351:211–214; Heim, R., et al. (1994) Proc. Natl. Acad. Sci., USA 91:12501–12504; Yang, T. T., et al. (1996) Nucleic Acids Res. 24(22): 4592–4593; Cormack, B. P., et al. (1996) Gene 173:33–38; Crameri, A., et al. (1996) Nature Biotechnol. 12:315–319; Haas, J. et al, (1996) Curr. Biol. 6:315–324; Galbraith, D. W., et al. (1995) Methods Cell Biol. 50:1–12; Living Colors Destabilized EGFP Vectors (April 1998) CLONTECHniques XIII(2) :16–17, Living Colors pEBFP Vector (April 1997) CLONTECHniques XII(2):16–17; Heim, R. & Tsien, R. Y. (1996) Curr. Biol. 6:178–182;

Ormö, et al. (1996) Science 273:1392–1395; Mitra, R. D. et al. (1996) Gene 173:13–17.

As used herein, the term "skin metabolism-related promoter" refers to a promoter which is transcriptionally active in the skin. It need not be skin-specific. The gene in which the promoter is naturally found can be a gene involved in the maintenance, or proper functioning of the skin. For example, the gene can be a gene encoding a protein which is part of the extracellular matrix, a protein involved in the maintenance or degradation of the extracellular matrix, or a protein involved in supplying nutrition to the skin. Active fragments or analogs of the promoters mentioned herein can be used in methods, compositions, and animals of the invention, e.g. an active fragment of the veriscan promoter. The 839 bp fragment of the functional human veriscan promoter (−559 to +280) (Naso, M. F. , Zimmermann, D. R. & Iozzo, R. V. (1994) *J. Biol. Chem.*, 269, 32999–33008) human genomic DNA can be used in methods which use a veriscan promoter.

Embodiments of the inventions allow for evaluation of transgene expression, in situ, on live animals. The luminescent or fluorescent reporters, e.g., GFP reporter molecule, are particularly advantageous in such embodiments.

As used herein, "administering a compound to an animal" refers to dispensing, delivering or applying a treatment to an animal or cell. Administration can be by topical administration, by parenteral or oral route, intramuscular injection, subcutaneous/intradermal injection, intravenous injection, buccal administration, transdermal delivery or administration by the intranasal or respiratory tract route. The most preferred administrations are topical application or subcutaneous or intradermal injection.

The methods of the invention allow rapid and efficient evaluation of compounds for their effect on skin.

Other features and advantages of the invention will be apparent from the following detailed description, and from the claims.

DETAILED DESCRIPTION

The drawings are first briefly described.

BRIEF DESCRIPTION OF THE DRAWINGS

Figure 3:
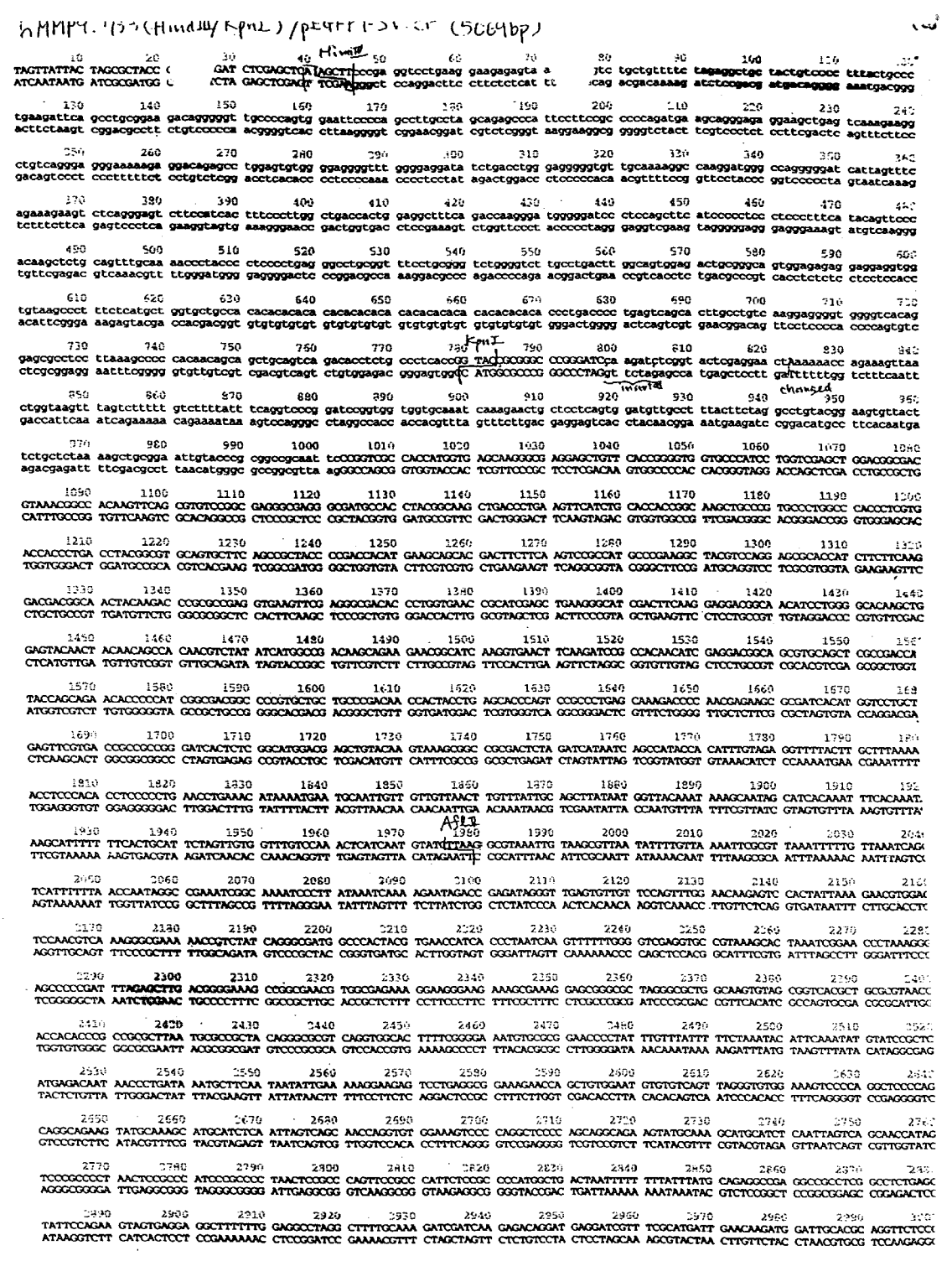
Figure 3:
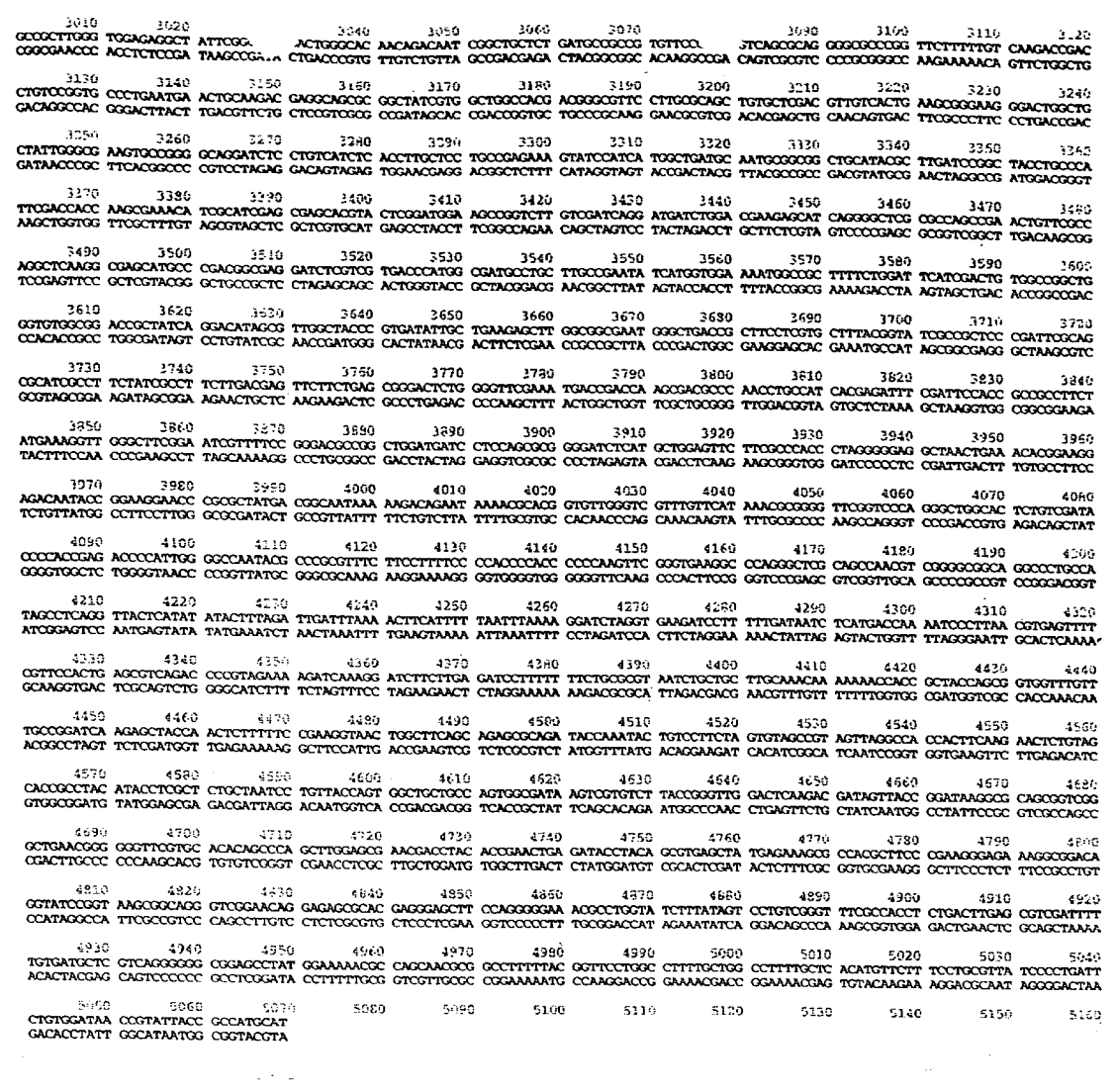

FIG. 3 is a depiction of the nucleotide sequence of the 5069 pb MMP9 promoter-GFP construct (coding and non-coding strand: SEQ ID NO: 1 and 2, respectively).

Figure 4:
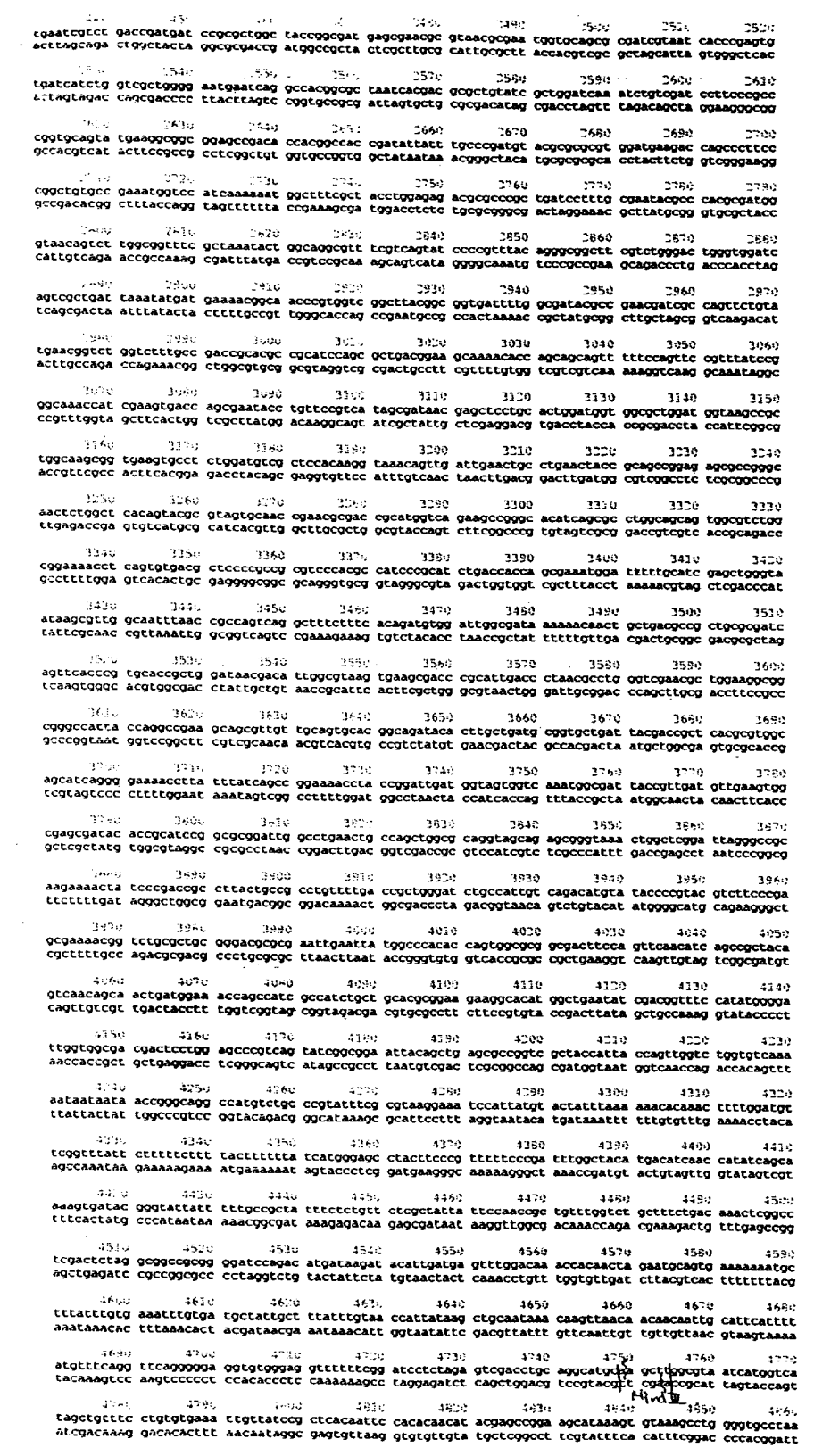
Figure 4:
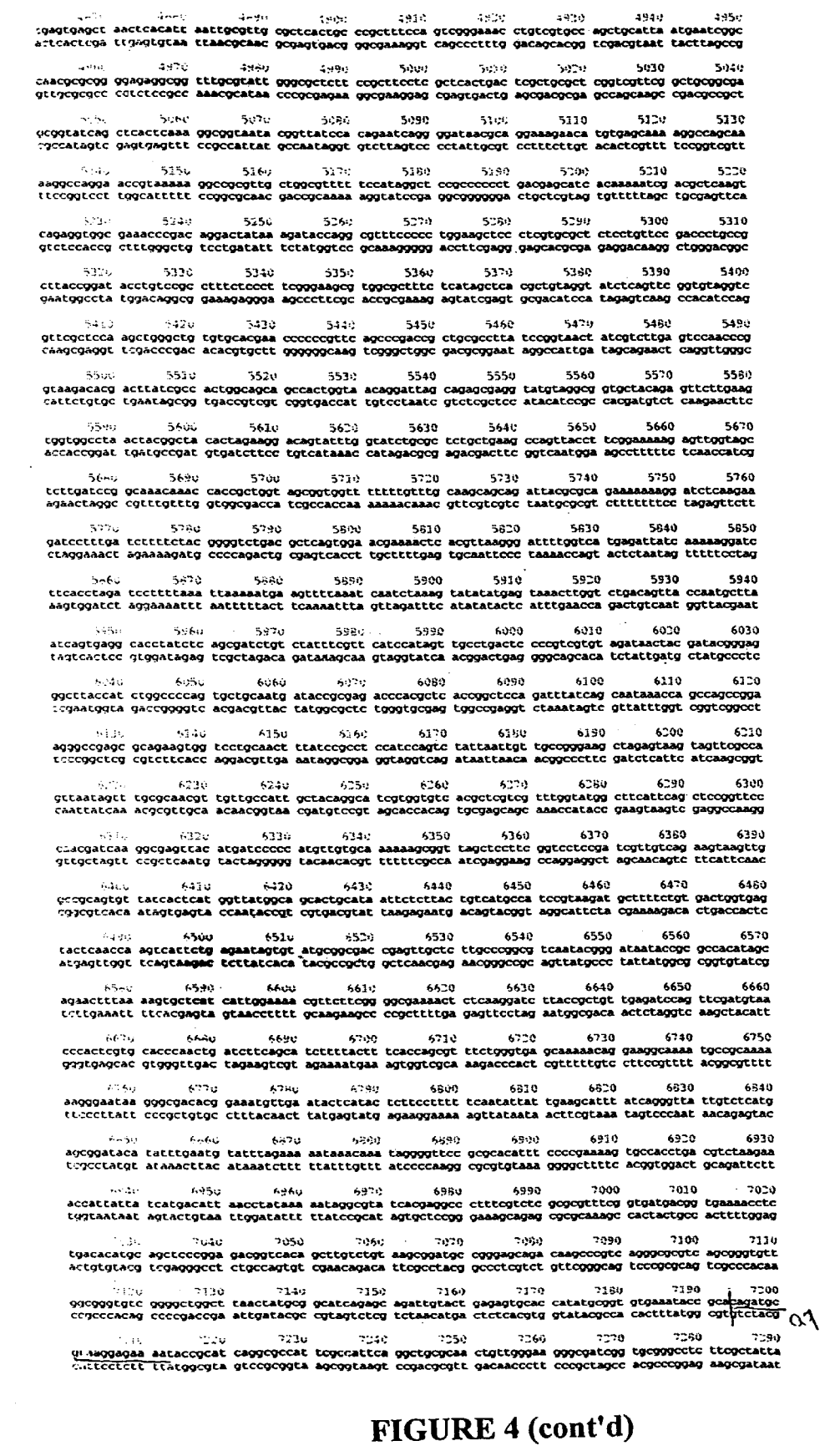

FIG. 4 is a depiction of the nucleotide sequence of the 7383 pb MMP9 promoter-beta-Gal construct (coding and non-coding strand: SEQ ID NO:3 and 4, respectively).

PROMOTERS

Figure 1:
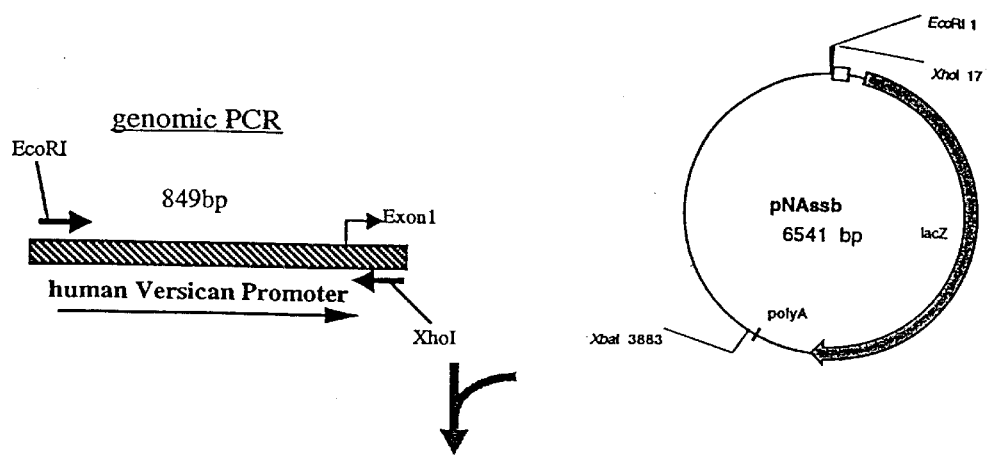
FIG. 1 is a schematic representation of the human versican-Lac Z transgene construction.
Figure 1:
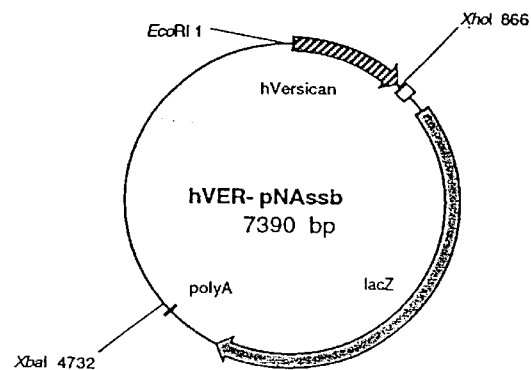
Figure 1:
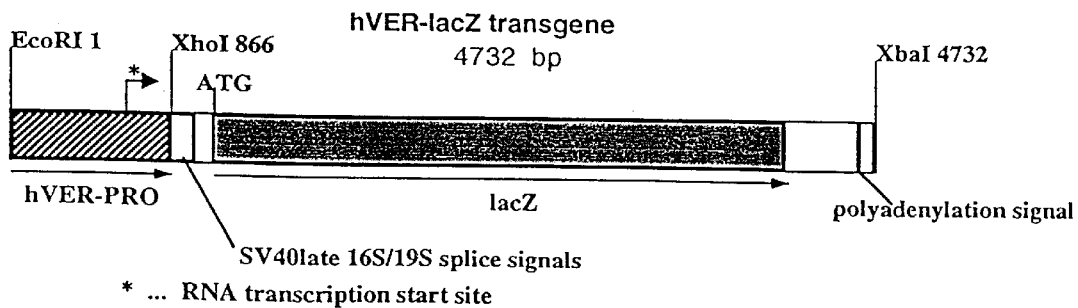

Methods of the invention allow evaluating a compound for its effect on the skin. Methods of the invention can be used to evaluate a compound for its effect on the health or appearance of the skin, e.g., for use as a cosmetic. The effect on skin is usually determined as an effect on the expression of a gene under the control of a skin-metabolism-related promoter. Such promoters include those which control the expression of: a product which is a component of the skin, e.g., the dermis or epidermis; a product which affects hydration or nutrition of the skin; a product which promotes the synthesis, or degradation, of components of the skin; a product which affects the vasculature of the skin; a product which affects hair follicle metabolism; a product which affects skin glandular structures; a product which affects subcutaneous musculature; a product which affects adipose tissue; or a product which affects cutaneous nerves.

Methods of the invention are useful for evaluating a compound for an effect on a parameter related to the appearance or health of the skin, for example, the elasticity of the skin, the propensity of the skin to wrinkle, the ability of the skin to retain fluids, e.g., water or an oil, the ability of the skin to resist or repair damage, e.g., light or UV induced damage, the metabolism of hair follicles including growth cycling or pigment deposition, subcutaneous muscle tone and function, or neurotransmission by cutaneous nerves. Generally, effects on these parameters will be evaluated indirectly, e.g., by the effect on the expression of a reporter gene under the control of a promoter which is normally coupled to a gene which encodes a product which affects any of the these parameters.

Examples of such skin-metabolism-related promoters include a versican promoter; a matrix metalloproteinase promoter; a vascular endothelial growth factor promoter; a hyaluronan synthase promoter; a MMP2 or MMP9, preferably a MMP9, promoter; and a neutrophil elastase promoter.

The versican promoter regulates the expression of the versican gene, described in Naso M. F. et al. (1994) *J. Biol. Chem.* 269(52): 32999–33008, the contents of which are incorporated herein by reference. Versican is a large modular chondroitin sulfate proteoglycan expressed in the dermis and the epidermis of the skin. Versican can bind large amounts of water while remaining attached to the extracellular matrix and can, therefore, hydrate and fill the skin. Accordingly, compounds which result in upregulation of this gene are preferred.

A matrix metalloproteinase promoter regulates the expression of a matrix metalloproteinase gene. The matrix metalloproteinases (MMPs) belong to a family of extracellular matrix proteases, described in Mauch C. et al. (1994) *Arch. Dermatol. Res.* 287:107–114. As the name implies, these matrix metalloproteinases are involved in the degradation of the extracellular matrix in, for example, the dermis and the epidermis of the skin. Accordingly, compounds which result in downregulation of this gene are preferred.

The vascular endothelial growth factor promoter regulates the expression of the vascular endothelial growth factor gene described in, for example, Tischer E. (1991) *J. Biol. Chem.* 266(18): 11947–11954, the contents of which are incorporated herein by reference. The vascular endothelial growth factor is a mitogen for vascular endothelial cells and, as a result, it can lead to proliferation of the microvasculature beneath the skin and increased vascular permeability. Increased microvasculature and vascular permeability allow for better nutrition (e.g., better nutrient delivery to the dermis and the epidermis) and hydration of the skin. Accordingly, compounds which result in upregulation of this gene are preferred.

The hyaluronan synthase (HAS1–3) promoters regulate the expression of the hyaluronan synthase (HAS1–3) genes, described in Itano N. et al. (1996) *BBRC* 222: 816–820; Watanabe K. (1996) *J. Biol. Chem.* 271(38): 22945–22948; and Spicer A. P. (1997) *J Biol. Chem.* 272(14): 8957–8961, respectively, the contents of which are incorporated herein by reference. Hyaluronan synthases, as the name implies, are enzymes involved in the synthesis of hyaluronan, a linear unbranched glycosaminoglycan. Hyaluronan binds versican and generally acts as an anchor for other proteoglycans, leading to the stabilization of the proteoglycan "network." As a result, hyaluronan (like versican) can assist in the hydration and filling of the skin. Accordingly, compounds which result in upregulation of this gene are preferred.

The type IV collagenase promoter regulates the expression of the type IV collagenase gene, described in Huhtala P. (1991) *J. Biol. Chem.* 266(25): 16485–16490, the contents of which are incorporated herein by reference. Type IV collagenase is another member of the extracellular matrix protease family and it is involved in the degradation of various components of the extracellular matrix in, for example, the dermis and the epidermis of the skin. Accordingly, compounds which result in downgulation of this gene are preferred.

The neutrophil elastase promoter regulates the expression of the neutrophil elastase gene, described in Takahashi H. (1988) *J. Biol. Chem.* 263(29): 14739–14747, the contents of which are incorporated herein by reference. Neutrophil elastase is a powerful serine protease capable of cleaving most protein components of the extracellular matrix (including elastin) in, for example, the dermis and the epidermis of the skin. Accordingly, compounds which result in downgulation of this gene are preferred.

Transgenic Animals

Transgenic animals which can be used in the methods of the invention include non-human mammals, such as pigs, e.g., mini-pigs, or guinea-pigs; or rodents, e.g., mice or rats, e.g., hairless mice (described in, for example, Begona M. et al. (1994) *Proc. Natl. Acad. Sci.* 91:7717–7721), nude mice, senescence accelerated mice (described in, for example, Takeda et al. (1991) *L. Am. Geriatr. Soc.* 39:911–19), or transgenic mutant mice which exhibit a phenotype of accelerated aging; in which one or more, and preferably essentially all, of the cells of the animal include a transgene. The transgenic animals can be homozygous or heterozygous for the transgene. Mice are a preferred subject animal.

Construction of Transgenic Animals

Methods of making transgenic animals, e.g., mice, are known in the art. One approach is described below.
Injection/Implantation of Embryos Procedures for embryo manipulation and microinjection are described in, for example, *Manipulating the Mouse Embryo* (Cold Spring Harbor Laboratory Press, Cold Spring Harbor, N.Y., 1986, the contents of which are incorporated herein by reference). Mouse zygotes can be collected from six week old females that have been super ovulated with pregnant mares serum (PMS) followed 48 hours later with human chorionic gonadotropin. Primed females are placed with males and checked for vaginal plugs on the following morning. Pseudo pregnant females are selected for estrus, placed with proved sterile vasectomized males and used as recipients. Zygotes are collected and cumulus cells removed. Furthermore, blastocytes can be harvested. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of a transgenic construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Recombinant ES cells can be injected into blastocytes, using similar techniques. Immediately after injection embryos are transferred to recipient females, e.g. mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.
Screening for the Presence of the Targeting Construct Transgenic animals can be identified after birth by standard protocols. DNA from tail tissue can be screened for the presence of the targeting construct using southern blots and/or PCR. Offspring that appear to be mosaics are then crossed to each other if they are believed to carry the targeting construct in their germ line to generate homozygous transgenic animals. If it is unclear whether the offspring will have germ line transmission, they can be crossed with a parental or other strain and the offspring screened for heterozygosity. The heterozygotes are identified by southern blots and/or PCR amplification of the DNA.

The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed as set forth above.

Other means of identifying and characterizing the transgenic offspring are known in the art. For example, northern blots can be used to probe the mRNA for the presence or absence of transcripts encoding the reporter gene. In addition, western blots can be used to assess the level of expression of the transgene in various tissues of these offspring by probing the western blot with an antibody against the protein encoded by the transgene, or an antibody against the marker gene product, where this gene is expressed. Finally, in situ analysis (such as fixing the cells and labeling with antibody) and/or FACS (fluorescence activated cell sorting) analysis of various cells from the offspring can be performed using suitable antibodies to look for the presence or absence of the transgene product.
Other Transgenic Animals Other transgenic animals can be used in methods of the invention. Methods for the preparation of a variety of animals are known in the art. A protocol for the production of a transgenic pig can be found in White and Yannoutsos, *Current Topics in Complement Research*: 64th *Forum in Immunology*, pp. 88–94; U.S. Pat. No. 5,523,226; U.S. Pat. No. 5,573,933; PCT Application WO93/25071; and PCT Application WO95/04744. A protocol for the production of a transgenic rat can be found in Bader and Ganten, *Clinical and Experimental Pharmacology and Physiology*, Supp. 3:S81–S87, 1996. A protocol for the production of a transgenic cow can be found in *Transgenic Animal Technology, A Handbook*, 1994, ed., Carl A. Pinkert, Academic Press, Inc. A protocol for the production of a transgenic sheep can be found in *Transgenic Animal Technology, A Handbook*, 1994, ed., Carl A. Pinkert, Academic Press, Inc. All patents and references are incorporated herein by reference.

Reporter Genes

The methods of the invention are based, at least in part, on coupling reporter genes to promoters of genes involved in skin metabolism. The reporter gene can be any gene which encodes a detectable product, preferably one which can be detected with relative ease, e.g., a gene product which is fluorescent, or which catalyzes a reaction which can be determined by formation of a colored product. For example, the reporter gene can encode an enzyme, e.g., an enzyme which produces a detectable product, e.g., a colored or a luminescent product. Reporter genes are known in the art and include a beta-galactosidase gene, a luciferase gene, a green fluorescent protein gene, an alkaline phosphatase gene, a horseradish peroxidase gene, or a chloramphenicol acetyl transferase gene. Reporter genes are described in, for example, Sambrook, J., Fritsh, E. F., and Maniatis, T.

*Molecular Cloning: A Laboratory Manual. 2nd, ed., Cold Spring Harbor Laboratory*, Cold Spring Harbor Laboratory Press, Cold Spring Harbor, N.Y., 1989.

EXAMPLES

Example 1

Construction of the Transgene

To construct the transgene, an 839 bp fragment of the human versican promoter (nucleotides −559 to +280; the transcription start site being +1) was obtained from human genomic DNA using art known PCR-based techniques. The versican promoter fragment was inserted into the pNASS2β vector (Clontech) which was linearized by restriction with XhoI-EcoRI as shown in FIG. 1. This vector contains the β-galactosidase reporter gene (lacZ) as well as a polyadenylation signal. This vector also includes an RNA splice donor and acceptor sequence to optimize the chance of high level of transgene expression. To obtain the linearized transgene DNA fragment for pronuclear injection, the vector was cleaved with an EcoRI and an XbaI enzyme. The linearized transgene DNA fragment has a length of 4732 bp.

Example 2

Generation of Transgenic Mice

The linearized transgene DNA fragment was injected into fertilized oocytes of DBA2×C57BL6 (DBFI) mice (Charles River, Boston), and the eggs were implanted into pseudopregnant foster mothers. The offsprings (F0) were tested for chromosome integration of the human versican promoter fragment by southern blotting. Briefly, genomic DNA was isolated from the tails of 3-week old mice and digested with either the BamHI or the PstI restriction endonuclease. The DNA fragments were separated on a gel and then transferred on a nylon membrane. The membranes were hybridized with a 1.3 BP BamHI-EcoRV fragment of the human versican transgene which was used to generate the transgenic mice. Seven independent lines showed transgene insertion by Southern analysis. The copy number of the transgene varied from one to more than ten.

Example 3

β-galactosidase Histochemistry

Collected mouse embryos of varying stages (from E11.5d to E17.5d) of development were fixed with 0.5% glutaraldehyde in PBS for 30 minutes to 12 hours, depending on the embryo stage, transferred to 30% sucrose, and then frozen in OCT (Tissue Tek, Calif.) compound. 15 μm-thick sections were prepared and loaded on slides. The sections were re-fixed in same fixative for 5 minutes and washed once with PBS, followed by a detergent wash solution for 10 minutes. Staining was performed in the reaction buffer containing 1 mg/ml X-gal (Sigma), 10 mM ferrocyanide, and 10 mM ferricyanide. Incubation was curried out for 3–6 hours at 37øC. After washing with PBS, sections were either mounted or counterstained with eosin. For adult tissue, mice were perfused with the same fixative and the desired organs were dissected and post-fixed, sucrose submerged, and then frozen with OCT compound. For skin tissue, 5 mm strips of back skin tissue block were fixed for 15 minutes to an hour and stained with X-gal, as described above for 3–6 hours. After washing, the skin tissue strips were embedded in paraffin and cut in 8 μm sections using a microtome.

Example 4

In situ hybridization

Radioactive in situ hybridization with 3' end labeled oligonucleotide probes was performed using methods known in the art. The specificity of the in situ signal was tested by hybridizing some sections with labeled oligonucleotides in the presence of excess unlabelled oligonucleotide.

The expression pattern of the transgene was examined by in situ hybridization of transgenic embryonic sections (E13.5) using lacZ and endogenous mouse versican probes. Using either probe, expression was observed in the developing limb bud, kidney, brain, and cartilage. LacZ expression was also examined by β-galactosidase histochemistry in E13.5, E15.5, E17.5 embryos, through 7-day, 40-day newborns, and 4 month (adult) transgenic mice sections. Strong mesenchymal expression was observed in the kidney, brain, cartilage, and limb bud, as early as E13.5d. The level of expression remained constant until birth. In 7-day old mice, the β-galactosidase staining was decreased compared to embryonic tissue and almost no expression was observed in adult tissue. In contrast to other tissue, dermal papilla (anagen hair cycle) from 30-day old mice exhibited intense β-galactosidase staining again and continued to express the same level of β-galactosidase during the second hair cycle.

In skin tissue, hair bud (future dermal papilla in hair follicle) expressed strong β-galactosidase activity at E15.5d and continued to do so until 7 days after birth (during the first hair cycle). Occasional β-galactosidase staining in dermal fibroblasts was also observed in El 5.5d-newborn skin. However, β-galactosidase staining was decreased in 7 day-old skin tissue.

Example 5

UV Irradiation

Irradiation with UVA was performed using a closely spaced array of five PUVA lamps. The energy output at 30 cm from array was measured with a UVA detector.

4-day old versican transgenic mice were irradiated on back skin with 30 J/cm2 UVA. Back skin tissue biopsy samples were processed 24 hours later for β-galactosidase staining and compared to untreated control skin from transgenic mice. β-galactosidase histochemistry showed increased β-galactosidase staining on the upper dermis of UVA irradiated skin compared to control.

Example 6

VEGF-GFP Transgenic Mice

Figure 2:
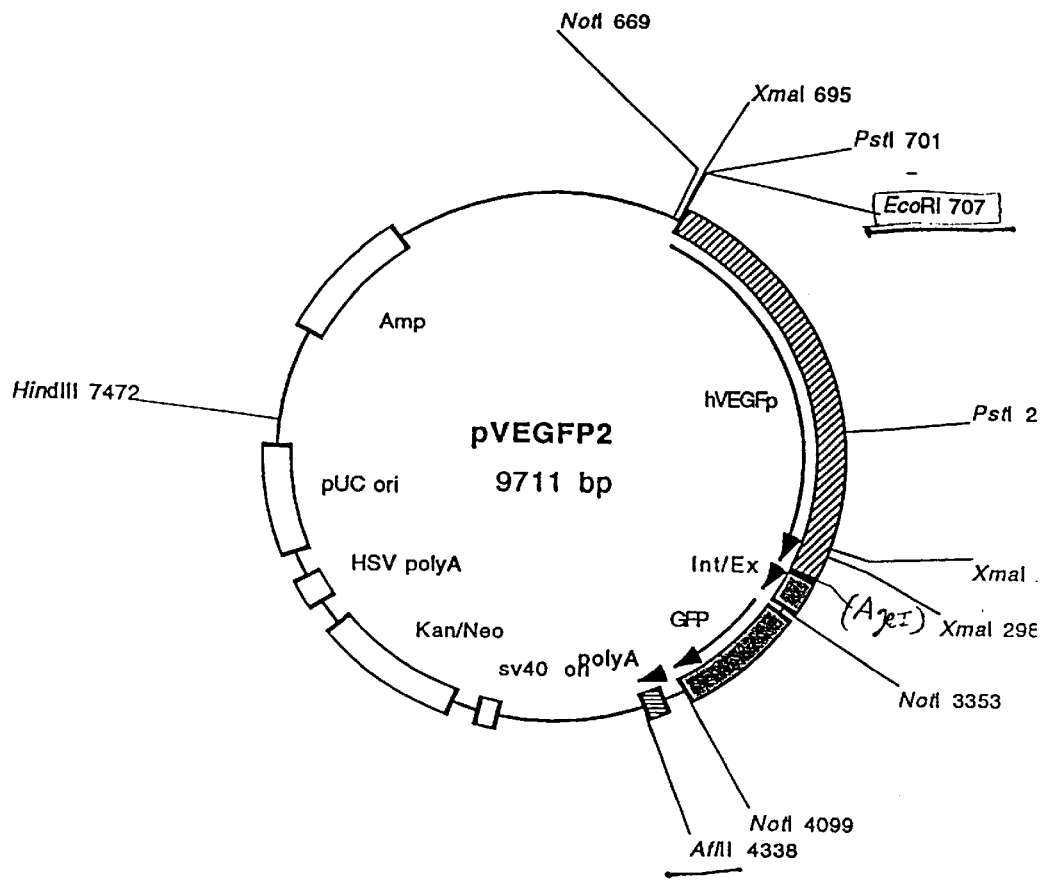
FIG. 2 is a schematic representation of the vascular endothelial growth factor-green fluorescent protein [VEGF-GFP] transgenic construct.

To elucidate the regulatory mechanisms of human VEGF gene expression in vivo, transgenic mice have been prepared which contain a green fluorescent protein reporter construct driven by a 3 kbp fragment of the promoter region of human VEGF (shown in FIG. 2). This construct was confirmed to be functional in vitro by transfection assays in cultured human keratinocytes. Three independent transgenic lines for VEGF-GFP were obtained and confirmed by PCR analysis. To examine constitutive endothelial expression, and keratinocyte inducible VEGF expression in wound skin, 2 mm skin punches were made in the back skin and biopsy samples were collected after 48 hours. Tissues were immediately fixed with 4% paraformaldehyde and cryostat sections were examined by fluorescent and confocal microscopy. VEGF-GFP transgenic lines exhibited bright GFP fluorescence in neomicrovascular networks beneath the epidermis and upper dermis, and occasionally in the deeper dermis. Hair follicles were also positive in some tissue. In wound tissue, continuous GFP expression was observed at the wound edge of the epidermis, but no keratinocyte expression was seen in non-wounded areas, confirming the inducibility of VEGF expression in healing wounds. Primary keratinocyte cultures prepared from the VEGF-GFP transgenic line also showed GFP fluorescence after 3 days in culture. Taken together these results indicate that GFP is a potentially useful tool to examine in vitro and in vivo VEGF expression. This work is described in more detail below.

Dynamic changes in the expression of green fluorescent protein driven by the human vascular endothelial growth factor promoter in transgenic mouse skin was analysed as follows.

Gene expression studies using transgenic mice most often utilize one of three classical reporter genes—lacZ (b-galactosidase) luciferase, or CAT (Chloramphenicol acetyl transferase). Detection of reporter gene activity usually requires the tissue to be removed from the animal for histochemical staining in the case of lacZ, or for complicated assays for luciferase and CAT, eliminating or at the least complicating the possibility of seeing a change in gene regulation in the living animal.

Recently an alternative fluorescent reporter molecule, green fluorescent protein (GFP), (Chalfee M, Tu Y, Euskirchen G, Ward W W and Prasher D C: Green fluorescent protein as a marker for gene expression. *Science* 263: 802–5, 1994) or modified GFP (EGFP), (Zhang G. Gurtu V and Kain SR: An enhanced green fluorescent protein allows sensitive detection of gene transfer in mammalian cells. *Biochem Biophys Res Commun* 227: 707–11, 1996) has been developed. Because GFP is intrinsically fluorescent, the signal is visible without treatment (Misteli T and Spector DL: Applications of the green fluorescent protein in cell biology and biotechnology. *Nat Biotechnol* 15: 961–4, 1997). When GFP is induced in the epidermis, it is possible to observe changes in gene expression without sacrificing the animals using confocal laser microscopy. The promoter of human vascular endothelial growth factor (VEGF), which is an angiogenic factor that induces in vivo angiogenesis and vascular permeability in malignant tumor tissue is used here to express GFP as a reporter gene in transgenic mouse skin. The expression of VEGF in epidermal keratinocytes was shown to be up-regulated at the edge of a healing epidermal wound, and also up-regulated topical application of phorbolesters, such as TPA.

The expression and responsiveness of GTP in signaling changes in gene activity of human VEGF-GFP in transgenic mice is described below. The expression patterns are consistent with that of endogenous VEGF, and show that GFP-derived fluorescent can be localized and visualized using confocal microscopy on intact tissue without any treatment following excisions.

Transgene Construct

Because PCR-based amplification of the GC-rish VEGF promoter is often difficult, a 5.0 kb fragment of VEGF genomic clone, which included the 5'-flanking DNA of human VEGF, was isolated from a human genomic library (Clontech, Calif.) using 500 bp cDNA fragment obtained by RT-PCR as a probe. The identified close was analyzed by restriction digestion, then a 2453 bp EcoRI-Agel fragment (−2271 to +91),(Tischer E, Mitchell R, Harman T, Silva M, Gospodarowicz D, Fiddes J C and Abraham J A: The human gene for vascular endothelial growth factor. Multiple protein forms are encoded through alternative exon splicing. *J. Biol Chem* 266: 11947–54, 1991) was excised from the agarose gell. This promoter fragment was inserted into a GFP vector (pEGFP-1 cut EcoRI and Xmal). To maximize the efficiency of expression, 16s/19s splice donor and acceptor'signals were also inserted between the promoter and GFP gene.

In Vitro Expression of GFP Vector.

The resultant transgene in the mammalian expression vector was first transfected into cultured human keratinocytes to confirm that the selected gene region promoted VEGF expression. Primary human keratinocytes were transfected with either the BEGF-GFP vector or a CMV promoter-driven GFP control vector (pEGFP-N1; Clontech). A porybrene and DMSO method was used for all transfections.

Generation of Transgenic Mice

The linearized fragment for pronuclear injection was excised with EcoRI and AflII, which also included a polyadenylation signal sequence. This transgene fragment was then injected into fertilized oocytes of DBA2×C57B16 (DBF1) mice (Charles River Laboratories, Boston, Mass.), and the eggs were implanted into pseudo pregnant foster mothers. The offspring (F0) were tested for chromosomal integration of the transgene by genome PCR. All experiments were done with F1 or F2 offspring mice.

For confocal microscopic observation of intact skin tissue, VEGF-GFP transgenic mice were generated in the hairless genetic background by breeding transgenic founder with SKH-1 hairless mice (Charles River Laboratories). Thus, male hemizygous transgenic mice (v/-HH) were mated with female hairless mice (-/-hh) to obtain the F2 generation of VEGF-GFP hairless mice (v/-hh), which could be easily selected by PCR detection and their hairless phenotype.

Tissue preparation for GFP detection and epimicroscopic observation solutions washed out or diffused GFP-derived fluorescence from the site of GFP expression. Ultimately, a freshly dissected, unfixed tissue block, was directly cut into 12 $\mu$m thick frozen sections using a cryostat. Epifluorescent microscopic observation was performed immediately after sectioning, without mounting medium or extended slide storage, using FITC/TRITC double excitation and an emission filter Chroma, *VT) to distinguish the GFP-derived fluorescent signal from tissue autofluorescence.

Wounding and TPA Treatment Procedure

Skin wounds were produced with a 2 mm biopsy punch on the shaved back skin of young adult transgenic mice aged 4–6 weeks old. After 48 hours, normal and wounded tissues were collected and immediately frozen on dry ice.

For induction of VEGF mRNA by TPA, a single dose of 5 $\mu$g TPA in acetone was topically applied to back skin of transgenic mice and skin biopsy samples were collected after 12 hours.

All animal procedures had the approval of the MGH Animal Care and Use Committee.

Anti-VEGF and Anti-GFP Immunohistochemistry

Cryostate sections of transgenic mice skin were fixed with 4% paraformaldehyde in PBS (pH 7.2) at room temperature for 5 min. Immunohistochemical staining was performed on slide mount sections using the ABC method as described by the manufacturer (Vector Labs. UK), and visualized by peroxidase reaction using DAB as a color substrate. Anti-GFP antiserum was purchased from Clontech.

Confocal Microscopy

For confocal microscopy observations, a coverslip was placed directly on the tissue. Sections or intact skin samples were analyzed using Leica TCS NT4D confocal microscope system with band pass filter 530/30 nm, detecting emission at wavelengths between 515–545 nm. To visualize nuclei, sections were counterstained with 5 µg/ml of 7-aminoactinomycin D(SIGMA, USA) solution for 20 min at ambient temperature, washed with PBS, and mounted with fluoromount-G (Southern Biotechnology, AL).

VEGF Promoter Driven GFP Expression in Human Keratinocytes

As the region of functional promoter activity for endogenous VEGF was not well characterized, 2.5 kb of 5'-flanking DNA of human VEGF was first inserted in a GFP mammalian vector and monitored in transfected primary human keratinocyte cultures. Control cultures were transfected with a CMV promoter-driven GFP vector, VEGF-GFP fluorescence was first visible at 48 hours after transfection, and only in a small percentage of the cells. CMV-GFP fluorescence was visible within 24 hours, and nearly all the cells were positive. The VEGF-GFP signal was similar in intensity to that of CMV-GFP control confirming that this construct is a functional in in vitro culture system. (Fluorescence in cultured keratinocytes transfected with human cytomegalovirus (CMV) immediate early promoter driven GFP as a positive control, and with VEGF-GFP, 48 hours after transfection were observed.)

Expression of GFP in Transgenic Mice

In 30 founder mice, four lines positive for transgene chromosomal insertion were detected by PCR analysis. Three of these lines showed detectable GFP-derived fluorescent signal in the epidermis as assessed by epifluorescence microscopy of tail tissue, compared with negative wild type mice. GFP expression in new born transgenic mouse (Fluorescence was determined in fresh, unfixed tissue from the tail from a VEGF-GFP transgenic mouse and a similar tissue from a negative wild-type litter mate. Fluorescence was also determined in tissues taken from new born VEGF-GFP transgenic mice: including lung (fluorescence seem in alveoli); lateral ventricle of the brain. (fluorescence was observed in lateral epithelium); and vertebral cartilage; (heart epithelium). The expression pattern of VEGF promoter was evaluated in F1 newborn pups of these three lines. The lung, kidney, and brain, previously been shown to express VEGF by in situ hybridization studies were chosen for examined for GFP fluorescence. As expected, GFP expression in lung alveoli and in the lateral ventricle wall in the brain was observed. It was difficult to detect a GFP signal in the flomerulus of kidney. GFP fluorescence was also detectable in the chondrocytes of developing cartilage tissue (e.g. vertebra cartilage).

GFP is Expressed at the Edge of Healing Wounds

Since non-stimulated, normal epidermal keratinocytes showed only weak GFP fluorescence, we tested the inducibility of VEGF-driven GFP during wound healing. 48 hrs after removal of a skin biopsy, the healing wound epidermis beneath the scab showed a very strong and distinct fluorescent signal compared with adjacent unwounded epidermis. This fluorescent signal correlated with VEGF/GFP expression detected by anti-GFP and anti-VEGF immunohistochemistry in adjacent sections. GFP expression induced by skin wound healing. (VEGF-GFP transgenic mice were wounded by punch biopsy. Tissue from the wound was taken for evaluation by fluorescence microscopy. (a) In healing wound edge 48 hours after biopsy strong fluorescence was observed in the epithelium underlying the scab. (b) An adjacent section was reacted with anti-GFP antibodies. (c) An adjacent section was immunostained with antimouse VEGF antibodies. A control section was treated with normal goat serum. Non-specific peroxidase staining observed in the scabs as also seen in b and c.)

Induction of GFP by TPA Treatment

Induction of epidermal GFP by phorbolester application was also examined. Accumulation of fluorescent signal was observed 12 hours after TPA was applied to transgenic skin, whereas acetone alone showed only basal levels of GFP expression. This signal seemed to localize to the basoplateral surface of the epithelium rather than in either the keratinocyt cytosol or nucleus. Anti-GFP immunostaining produced a signal in the basal cell cytosol, indicating that GFP originated in basal cells, and at least part of the GFP protein remained within the cell.

Direct Detection of GFP by Confocal Microscopy

In order to localize the GFP fluorescence signal more precisely, fresh cryostat sections were fixed and incubated with 7-AAD for nuclear counter staining and examined under laser confocal microscope. As expected, most diffusable GFP was lost during this procedure, although wound healing-induced-epidermal expression remained unaffected. Occasional fluorescence was detectable in the unwounded epidermis, where the fluorescence appeared to localize outside basal cells as we observed. Even after fixation and intense washing, GFP-derived fluorescence in the outer root sheath of hair follicle remained unchanged. At higher magnification of the hair follicles, it can be seen that the fluorescent GFP signal completely co-localized with a nuclear maker, indicating that hair follicle GFP remains stably within the nucleus. This was also the case for the chonodrocytes in the vertebrae cartilage.

Direct Detection of GFP in the Epidermis of Intact Skin by Confocal Microscopy

To test the possibility that GFP might be detected in the skin of a living GFP transgenic mouse, dissected hairless skin was directly examined by confocal imaging. Horizontal optical sections of the living epidermis revealed bright fluorescence. The equivalent cryostate section showed that this fluorescence is derived from the basal cells. Higher magnification revealed that GFP was localized in the extracellular space around the keratinocytes. X–Z confocal imaging confirmed that this signal was within the basal layer of the epidermis. Detection of GFP expression in intact skin by confocal microscopy. Fress unfixed transgenic mouse skin was biopsied, and immediately evaluated by scanning laser confocal microscopy. Horizontal optical sections of the epidermis show fluorescence surrounding individual epithelial cells. Cryostate sections of an equivalent skin region counterstained with 7-AAD to indicate nuclei, showed fluorescence at the dermal-epidermal junction. The confocal X–Z image indicates the fluorescence near the basal keratinocytes.

This work shows that the expression pattern of GFP driven by a human VEGF promotor is spatially and temporally equivalent to that seen with mRNA detection.

Pups from breedings of transgenic mice expressing GFP in the skin epidermis were easily selected by simple epifluorescent microscopy, without the more tedious procedures of southern blotting or genomic PCR.

There was initial difficult in detecting GFP-derived fluorescence in sections, even though fresh untreated tissue blocks emitted bright fluorescence. After testing a variety of procedures, it was found that aqueous solution treatment immediately washed out the GFP flourescence. This was partially overcome by fixing the tissue block before cryostate sectioning, though fluorescence from some sites, such as that initially present in epidermal keratinocytes, was still lost or its staining pattern was altered. Fixation induced fluorescence indistinguishable from that produced by GFP in the skin microvasculature. Fluorescence at this site was not seen in unfixed tissue, and VEGF expression has not been reported in the microvasculature in studies using in situ hybridization methods. Thus, the most efficient method to preserve the original GFP signal is to immediately cryostat section freshly dissected skin without OCT compound, and then promptly examine it by fluorescence microscopy. This unexpected difficulty may explain why, until now, there have been so few reports of successful GFP transgenic mice.

Prominent VEGF expression has been reported in lung, and in the lateral ventricle of the brain by in situ hybridization. Evaluation of the VRGF-GFP mice tissues confirm these findings. Failure of the kidney glomeruli to fluoresce may be due to a lack of tissue specific response element to 2.2 kb of 5'-flanking region of VEGF DNA used here for generating these transgenic mice, or to a signal below the detection threshold.

In skin from a 1 week old pup, normal epidermal keratinocyte showed basal levels of GFP expression, while bright fluorescence was observed in the outer root sheath of hair follicle. The skin of older mice did not show equivalent GFP expression in hair follicles, therefore, VEGF expression in the follicles may be hair cycle-dependent. Fluorescence in hair follicle and in chondrocytes, as seen in the vertebra and previously reported was particularly impressive. These signals were even stronger than those observed in lung or brain. Laser confocal observations revealed that GFP at these locations is confined within the nuclei. This nuclear localization may intensify the apparent signal since nuclear localization is likely to reduce the diffusion of the fluorescent product during tissue processing. The reason for localization to the nucleas by some tissues and not by others remains unexplained, but suggests that inclusion of a nuclear localization consensus sequence with in the transgene might be useful.

The inducibility of GFP protein during wound healing model and after TPA treatment is shown herein, confirming that the reporter GFP expression pattern is highly VEGF promoter-dependent. Also, these data eliminated concerns about the possible delay in fluorescent signal production due to slow chromophore formation as reported in Drosophila embryos. (Davis I, Girdham CH, O'Farrell PH "A nuclear GFP that marks nuclei in living Drosophila embryos; maternal supply overcomes a delay in the appearance of zygotic fluorescence" Dev. Biol. 170:726–9 (1995)). In anticipation of this difficulty the red-shifted variant of GFP was selected for these studies, and the correct folding of the chromophore appears to occur in skin as well as in more internal tissues. There was also concern that GFP might have a prolonged half life in skin interfering with the ability to use the reporter to monitor long-term gene expression. The disappearance of fluorescence in hair follicles of older transgenic mouse skin indicates that GFP protein has a reasonable half life.

Laser confocal microscopic evaluation of intact skin for detection of the GFP signal indicates that GFP is readily detected within the epidermis. These results suggest the potential use of GFP transgenic mice for non-invasive monitoring of long-term gene expression in vivo. The technology for microscopic evaluation of living mouse skin is already in use. When combined with use of a transgenic GFP reporter gene, the system has a great advantage over conventional transgenic reporter gene animals methods because it reduces the number of animals used, utilizes a simple monitoring system, and allows long term monitoring of changes in gene expression on the same individual. Our successful in vivo expression of GFP in transgenic mouse skin should facilitate the understanding of VEGF gene expression in skin, by providing a useful monitoring and screening tool. Its use would be particularly attractive when bred to a mouse with a phenotype thought to involve VEGF expression. This model would also be advantageous in research focused on skin homeostasis during the aging process.

Example 7

Developmental and Age-Related Changes of Human Versican Promoter Activity in Transgenic Mice Skin and Hair Dermal Papilla To investigate further for temporal-spacious expression pattern for human versican, particularly in skin tissue, transgenic mice were generated containing a lacZ reporter construct driven by the functional promoter for the core protein of human versican and tissue sections from resultant transgenic mice ranged from embryos, newborn to adult stage were examined by b-galactosidase histochemistry.
Construction of Transgene The 839 bp fragment of functional human versican promoter (from −559 to +280 according to the transcription start site as +1) including exon 1; (Naso MF, Zimmermann DR and Iozzo RV, "Characterization of the complete genomic structure of the human versican gene and functional analysis of its promoter", J. Biol. Chem. 269:32999–3008 (1994)) was obtained from human genomic DNA by PCR based technique and correct sequences were confirmed by direct sequencing. pNASS2βvector (Clontech) was used as a source of β-galactosidase reporter gene (lacZ) with polyadenylation signal. This vector also included RNA splice donor and acceptor sequence to optimize the chance of high level of transgene expression. Versican promoter fragment was inserted in front of splice donor/acceptor sequence using XhoI-EcoRI restriction site. Linearised transgene DNA for pronuclear injection was obtained as EcoRI-Xbal 4732bp fragment.
Generation of Transgenic Mice The linearized construct was injected into fertilized oocytes of DBA2×C57BL6(DBF1) mice (Charles River, Boston), and the eggs were implanted into pseudo pregnant foster mothers. The offspring(F0) were tested for the chromosome integration of the human versican promoter construct by Southern hybridization. Thus, genomic DNA was isolated from the tails of the mice at 3 weeks old and digested either BamHI or PstI restriction endonuclease. The fractionated DNA fragment on the nylon membranes were hybridized with 1.3kbp BamHI-EcoRV fragment of human versican transgene were used to generate transgenic mice. Seven independent lines which show transgene insertion by Southern analysis with different copy number from single insertion to more than ten.
b-galactosidase Histochemistry Collected mouse embryos of early to mid stages (from E11.5d to E15.5d) of development were fixed with 0.5% glutaraldehyde in PBS for 30 min to 12 hrs depends on the stage and transferred to 30% sucrose, then frozen in OCT compound. Sections were cut 15 um thickness and loaded on slides. Sections were re-fixed in same fixative for 5 min and was once with PBS, followed by detergent wash solution for 10 min. Staining reaction was done in the reaction buffer containing 1 mg/ml X-gal (Sigma), 10 mM ferrocyanide, and 10 mM ferricyanide. Incubation was curried out for 3–6 hrs at 37° C. After washing with PBS, sections were either mounted or counterstained with eosin. For adult tissue, mice were perfused with same fixative and desired organs were dissected and post-fixed, sucrose submerged, then frozen with OCT compound. In order to preserve better morphology some early to mid embryo (from E11.5d to E15.5d) were processed for paraffin section. For skin tissue, 5 mm strip of back skin tissue block were fixed for 15 min-1 hr and proceed X-gal staining for 3–6 hrs. After wash, blocks were processed for paraffin embedding and cut 8 um section with microtome.

In Situ Hybridization

The embryo tissues for in situ hybridization were fixed freshly prepared 4% paraformaldehyde in DEPC-treated PBS, dehydrated, processed through a standard paraffin embedding protocol under RNase-free condition. Digoxigenin labeled non-radioactive in situ hybridization was performed on 8 um paraffin sections of E13.5d embryo as described previously (Kishimoto J, Cox H, Deveme E B, and Emson P C "Cellular Localization of Putative Odorant Receptor Messenger RNAs in Olfactory and Chemosensory Neurons—A Non Radioactive Insitu Hybridization Study" *Molecular Brain Research* 23:33–39 (1994)). CDNA for lacZ and mouse versican antisense probe were prepared by PCR and sub-cloned into pBluescriptII(stratagene). Digoxigenin labeled RNA probes were prepared using a RNA labeling kit (Boehringer) according to the manufacturers' instruction. Paraffin sections on slides were quickly dewaxed in xylene, dehydrated through 100%, 90%, 70% ethanol, washed with 0.1M PBS (pH7.5) and then treated with 0.2N hydrochloric acid for 10 minutes. Sections were treated with 0.02% pepsin (in 0.2N HCl) for 30 minutes at 37° C., following which the enzyme was deactivated by 4% paraformaldehyde. After rinsing in 0.2% glycine solution (in PBS) three times, slides were acetylated in 0.25% acetic anhydride in 0.1M triethanolamine/0.9% NaCl for 10 minutes at room temperature and partially dehydrated through 70, 80, 90% ethanol and briefly dried. Approximately 0.1 µg/ml digoxigenin labeled RNA probes (denatured by boiling prior to use) were added in hybridization buffer (50% deionized formamide, 4XSSC, 10% dextran sulphate, 1X Denhardt's solution) and slides were incubated at 55° C. under coverslips for 16–18 hours. The coverslips were carefully removed and the sections were washed in 2XSSC/0.1% SDS for 30 minutes at room temperature, sequentially washed twice in 0.1XSSC/0.1% SDS at 60° C. for 30 minutes. Immunohistochemical procedures to visualize the hybridized probes used alkaline phosphatase conjugated anti-manufactures' instructions. The colorimetric reaction was started by adding nitroblue tetrazolium (Boehringer) and 5-bromo-4-chloro-3-indolyl-phosphate (Boehringer) and incubated for 6–24 hours at room temperature. Slides were mounted with glycerin jelly and were kept at 4° C.

Radioactive in situ hybridization with 3' end labeled oligo nucleotide probes was carried out as described previously (Kishimoto J. Keverne E B, Hardwick J, Emson P C, "Localization of nitric oxide synthase in the mouse olfactory and vomeronasal system: a histochemical, immunological and in situ hybridization study" *European J. of Neuroscience* 5:1684–1694 (1993)). Sequences of mouse versican antisense oligonucleotide probes were 5'-CCGTTCTGGGCCACCAAGACAGTCGTCTCC-3' (SEQ ID NO:5), 5'-TGACCGCCCCGATATCCAAACAAGCCTGTT-3' (SEQ ID NO:6), 5'-TCCGACAGCCAGCCGTAATCGCATTGGTCA-3' (SEQ ID NO:7). Some sections were hybridized with labeled oligonticleotides in the presence of excess unlabelled same oligonucleotides to check the specificity of the in situ signal.

Cell Culture

For primary fibroblast culture from transgenic mice skin, newborn transgenic mice skin were pealed off and incubated in 0.25% trypsin 18 hrs. Discarded epidermal sheet and dermis were further digested by collagenase for 1 hr. Cells were spread out to the MEDM medium (GIBCO)+10% FCS. cells were passaged in every 3 days after trypsin treatment. For b-galactosidase histochemistry cultured fibroblast cells were fixed with 0;.2% glutaraldehyde in PBS for 2 min., followed by detergent wash solution for 5 min. and 15 staining reaction was performed for 18 hrs. at 30° C. After reaction was stopped cells were proceeded for counter-nuclear staining with 5 µg/ml of 7-aminoactinomycin D (SIGMA, USA) solution for 20 min. at R. T. then, washed PBS, mount with fluoromount-G (Southern Biotechnology, Ala.).

Generation of Hairless Versican-lacZ Transgenic Mice

To eliminate hair follicle derived lacZ expression in order to examine age-related change of versican promoter activity, hairless genetic background of versican-lacZ transgenic mice were obtained by breeding with SKH-1 hairless mice resultant founder with SKH-1 (Charles River Laboratories, Boston). Thus, male hemizygous transgenic mice (v/-HH) were mated with female hairless mice(-/-hh), and selected transgene positive pups (v/-Hh) by genomic PCR were then mated back to a hairless again to obtain some F2 generation of versican-lacZ hairless mice(v/-hh) which can be easily selected by combination of PCR detection and hairless appearance.

Generation of Versican-lacZ Transgenic Mice

Of a total of 27 founder mice six positive lines were detected by both PCR and southern blotting analysis for the transgene insertion. The copy number of transgene was 1 to more than 20 copies per cell. These were further screened for lacZ staining by using X-gal histochemical reaction on tail skin. The intensity of lacZ staining in tail did not correlated with the copy number of transgene as both two lines. A4681(1–2 copies) and A4688(over 20 copies) exhibited similar strong lacZ staining in tail hairs with A4679 which had also over 20 copies, showed only light staining in tail. The transgenic line A4681 was chosen for further study as the staining of tail skin was most intense and had a good breeding behavior. All further analysis was performed on F1 –F3 offspring derived by mating with DBA/2 strain.

Distribution of LacZ Expression in Embryonic Tissue

Intense lacZ staining was observed in developing fore and hind limb (E13.5) within an area of mesenchymal condensation and also in ectoderm. This ectodermal expression was restricted in the tip of limb. In situ hybridization with radio-labeled antisense oligoes showed similar endogenous mouse versican mRNA expression in condenses mesenchyme in limb bud.

In E15.5 embryo strong lacZ staining was also observed in kidney glomeruli mesenchyme in olfactory epithelium, mesenchyme and muscles in tongue, and submandibular gland. Perichondrocyte surrounding cartilage, blood vessel, developing edge of hind and fore brain, smooth muscle were also positive.

The expected expression pattern other than limb was confirmed by digoxigenin non-radioactive in situ hybridization with lacZ and endogenous mouse versican probes on transgenic embryonic section (E13.5) as well as control sense probes. Both mRNA expression was observed in, kidney, olfactory epithelium, humerus cartilage, and in vertebrae cartilage, confirming reasonable expression pattern and timing of expression of this transgenic mice.

Human Versican Activity in Embryonic Skin

LacZ expression was examined by X-gal histochemistry on developing skin from E13.5, E14.5, E15.5 and E17.5 embryo. At E13.5d basically no staining was observed in whole body of ectoderm except hind and fore limb and with a few occasion trace of lacZ staining was found in single mesenchymal cell which seems to be earliest stage of condensation. Hair germ of whisker has already exhibited lacZ staining at this stage. At E14.5 condensed mesenchymal cells attached beneath ectodermal placode (hair plug) were clearly lacZ positive and this was highly contrasted against complete negative surrounding scattered mesenchymal cells. Phase contrast photo showed individual b-gal positive condensed mesenchymal cell. The number of these positive site were 4–5 per sagittal—mediaeval embryonic section of whole embryo tissue. At E15.5 these positive condenses mesenchyme under hair plug were getting more intense and increased in volume (i.e. the number of cell). At E17.5 the number and intensity of lacZ positive dermal papilla are dramatically increased, yet still highly restricted within the future dermal papilla. A few epidermal placode (i.e. epithelial keratinocytes) itself exhibited lacZ staining although the majority were still restricted in mesenchymal cells.

Hair Cycle Dependent Human Versican Activity in Transgenic Mice Skin

LacZ staining was examined on the skin section of transgenic mice from newborn, 7 days, 14 days, 28 days, 40 days, to 4 month old. Strong lacZ staining in hair dermal papilla cells in late embryonic skin were proceed into new born skin and continue during first anagen hair cycle. Strong staining was confined within the dermal papilla cells. Interestingly at age 7, mid to late anagen stage relatively strong staining was also observed in inner root sheath. However, in late anagen stage lacZ staining was again restricted only in dermal papilla cells. Also later in telogen hair no lacZ staining observes in club hair. In second hair cycle growing dermal papilla (second anagen hair cycle) exhibited again intense lacZ staining and after second anagen hair cycle lacZ activity in hair dermal papilla was decreased almost completely through long telogen hair cycle.

Human Versican Activity in Cultures Fibroblast

Primary dermal fibroblast culture derived from dermal fibroblast cells of new born transgenic line exhibited lacZ staining in only certain population of cells and center of hair clamp, obviously dermal papilla. Since all strongly stained cells were round shape these should be derived hair dermal papilla. After first passage, however, shape of positive cells were diversed and not confined round shape, including typical fibroblast-like cells with dendritic process in passage 2. These population of positive cells maintained after first passage to at least until six passages we cultured while certain number of cells were completely unstained through passages determined with counter-nuclear staining which clearly indicated total number of cells. Approximate number of positive cells were not exceed over 50%. Intensity of staining was gradually faded with passages.

Age-related Change of Human Versican Activity in Transgenic Mouse Skin

Increasing reaction time for x-gal staining to 18 hrs revealed more staining in upper dermis other than hair dermal papilla in young to adult skin of the transgenic mouse. In newborn mouse skin under this long incubation condition, most of dermis including hair follicle (hairless mouse have normal hair only in first cycle) showed fairly detectable staining. Young mouse skin showed only isolated fibroblast derived diffused staining preferentially in upper dermis, and older mouse only exhibited faint staining, indicating age-related decrease of human versican promoter activity in transgenic mouse skin.

Example 8

Evaluation of Reporter Gene Expression in a Live Animal.

Method:

Confocal Microscopy

To examine whole intact skin on living transgenic mouse with confocal microscope, hairless VEGF-GFP transgenic mice were anaesthetized with avertin by intraperitoneal injection. They were placed directly on the petri dish with dorsal position. TPA or acetone treatment was performed on the back skin same as described above marking treated area with an ink to ease the orientation of the skin. Sections or intact skin of the mice were analyzed using Leica DM IRBE inverted microscope and Leica TCS NT4D confocal microscope system with band pass filter 530/30 nm, detecting emission at wavelengths between 515–545 nm.

Direct Detection of GFP in the Epidermis of Intact Skin of Living Hairless Transgenic Mice by Confocal Microscopy To test whether the induction of GFP is directly detected in the skin of a living VEGF-GFP transgenic mouse, acetone or TPA applied skin of the transgenic hairless mouse (same individual) was directly examined by confocal imaging under anaesthetized condition. Horizontal optical sections through the normal living epidermis revealed detectable fluorescence and the skin treated with TPA after 12hrs showed the increase of fluorescence positive area. Non-transgenic wild type litter mate showed no detectable specific fluorescence. Higher magnification of the TPA treated skin revealed that GFP was localized in the extracellular space around the keratinocytes. X–Z confocal imaging confirmed that this signal was within the basal layer of the epidermis.

Laser confocal microscopic evaluation of an intact skin of living transgenic mouse for detection of the GFP signal indicates that GFP is readily detected within the epidermis. These results suggest the potential use of GFP transgenic mice for non-invasive monitoring of long-term gene expression in vivo. When the transgenic GFP reporter gene is combined with the technology for microscopic evaluation such as confocal microscope, the system has a great advantage over conventional transgenic reporter gene animals methods because it reduces the number of animals used, utilizes a simple monitoring system, and allows long term monitoring of changes in gene expression on the same individual.

Successful in vivo expression of GFP in transgenic mouse skin provides for the understanding of the regulation of VEGF gene expression, such as in inflammatory and neoplastic skin diseases, by providing a useful monitoring and screening tool. It is particularly attractive when bred to a mouse with a phenotype which involves VEGF expression. This novel experimentation model will allow in vivo studies on the regulation of VEGF gene. This GFP reporter system on transgenic animal would also be advantageous in research focused on skin homeostasis during the aging process.

Example 9

Human MMP9 Transgenic Mice

MMP9 (gelatinase B, 92-kDa type IV collagenase) is one of the member of matrix metalloproteinases (MMPs) capable to degrade extracellular matrix (ECM) components. This enzyme (MMP9) is known to degrade type IV and V collagens, gelatin and elastin. It is also shown to be induced by UVB which causes photoaging. (Fisher, G. J., *Nature*

379, 335, 1996). 5'flanking region of this gene from −670 sequence position to +1 transcription start site is sufficient to drive expression of a reporter gene (CAT) in HT1080 cells. (Sato, H., *Oncogene* 8, 395, 1993).

Construct of the Transgene

To construct the transgene, an 733 bp fragment of the human MMP9 promoter (nucleotides −714 to +19; the transcription start site being +1) was obtained from human genomic DNA using art known PCR-based techniques. Two different reporter genes, beta-galactosidase reporter gene (lacZ) and green fluorescent protein (GFP) gene, were employed for construction.

For the construction with beta-galactosidase reporter gene (lacZ), the MMP9 promoter fragment was inserted into an modified pNASSbeta vector (Clontech), which is inserted neutrophil elastase promoter and has Bgl II site, linearized by restriction with Bgl II-Xho I. To obtain transgene DNA fragment for pronuclear injection, the vector was cleaved with Bgl II and Hind III. The length of the linearized transgene DNA was 4630 bp.

For the construction with green fluorescent protein (GFP) gene, the same MMP9 promoter fragment was inserted into the pEGFP-1-SV, which was modified vector to have splice donor/acceptor based on pEGFP-1 vector (Clontech), linearized by restriction with Hind III-Kpn I. To obtain transgene DNA fragment for pronuclear injection, the vector was cleaved with Hind III and Afl II. The length of the linearized transgene DNA was 1928 bp.

Generation of Transgenic Mice

The lenearized transgene DNA fragment was injected into fertilized oocytes of hairless mice (SKH1; Charles River, Boston). Those eggs were implanted into pseudo pregnant foster mothers. The offsprings (F0) were tested for chromosome integration of lacZ or GFP fragment by southern blotting. For the detection of lacZ transgene, the genomic DNA extracted from the tail was digested with Nci I and separated on a gel, then transferred on a nylon membrane. The Nci I digested transgene DNA fragment was used for the probe. Two independent lines showed a transgene insertion. For the detection of GFP transgene, the tail genomic DNA was digested with Hinc II Two independent lines showed a transgene insertion.

Beta-galactosidase Histochemistry

F1 mice obtained from founders (F0) were used for beta-galactosidase histochemistry. Bones of 2-wk-old mice hindlimb were fixed with 0.5% glutaraldehyde in PBS for 30 minutes. After three times washing with PBS and once with detergent wash, the tissue was incubated with reaction buffer containing 1 mg/ml X-gal (Sigma), 10 mM ferrocyanide and 10 mM ferricyanide at 37° C. After 2 hours incubation, blue staining was observed in a F1 mouse which has transgene, while no staining was observed in the sibling without transgene. These are consistent with a report in which MMP9 was shown to express at bone of 2-wk-old mouse limb by in situ hybridization (Reponen, P., Journal of Cell Biology 124, 1091, 1994).

Example 10

Human Neutrophil Elastase Transgenic Mice

Neutrophil elastase is one of the powerful serine proteinase capable attacking a broad range of proteins. Hairless mice deficient in this enzyme do not suffer from elastosis, which is one of signs of photoaging caused by UVB irradiation. (Starcher, B., *Connective Tissue Research*, 31, 133, 1995). Therefore, neutrophil elastase is believed to play an important roll in photoaging.

Construction of the Transgene

To construct the transgene, an 1299 bp fragment of the human neutrophil elastase promoter (nucleotides −1280 to +19; the transcription start site being +1) was obtained from human genomic DNA using art known PCR-based techniques. This neutrophil elastase promoter fragment was inserted into the pNASSbeta vector (Clontech) linearized by restriction with Eco RI-Xho I. To obtain transgene DNA fragment for pronuclear injection, the vector was cleaved with EcoR I and Xba I. The length of the linearized transgene DNA was 5171bp.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of evaluating a compound for its effect on skin, comprising:

providing a live transgenic mouse whose genome comprises a nucleic acid sequence encoding a reporter polypeptide coupled to a promoter selected from the group consisting of: a vascular endothelial growth factor (VEGF) promoter, and a versican promoter, wherein the reporter polypeptide is expressed in the skin of the mouse, and wherein the reporter polypeptide is a luminescent or fluorescent product;

administering the compound to the transgenic mouse; and evaluating expression of the nucleic acid sequence encoding the reporter polypeptide in the skin of the live transgenic mouse while the skin is still on the mouse, wherein an alteration in expression of the nucleic acid sequence encoding the reporter polypeptide after administering the compound as compared to expression of the nucleic acid encoding the reporter polypeptide prior to administering the compound is indicative of an effect on skin, thereby evaluating the compound for its effect on skin.

2. The method of claim 1, wherein the compound is applied to the skin of the transgenic mouse.

3. The method of claim 1, wherein the reporter polypeptide is green fluorescent protein or modified variants thereof.

4. The method of claim 1, further comprising a repeating the administering step.

5. The method of claim 1, wherein the evaluating step is repeated at least once during the life of the mouse.

6. The method of claim 5, wherein the evaluating steps are separated by as much as 1, 10, 30, 60, 90, 180, 365, or 700 days.

7. The method of claim 3, wherein the modified variant of green fluorescent protein is selected from the group, consisting of EGFP, EBFP, EYFP, d2EGFP, and GFPuv.

8. The method of claim 1, wherein the promoter is a vascular endothelial growth factor promoter.

9. The method of claim 1, wherein the promoter is a versican promoter.

10. The transgenic mouse of claim 7, wherein the promoter is a VEGF promoter.

11. A transgenic mouse whose genome comprises a nucleic acid sequence encoding a reporter polypeptide coupled to a promoter selected from the group consisting of: a vascular endothelial growth factor (VEGF) promoter and a versican promoter, wherein the reporter polypeptide is expressed in the skin of the mouse and the reporter polypeptide encodes a luminescent or fluorescent product.

12. The transgenic mouse of claim 7, wherein the promoter is a versican promoter.

13. The transgenic mouse of claim 7, wherein the reporter polypeptide is green fluorescent protein (GFP) or a modified variant thereof.

14. The transgenic mouse of claim 7, wherein the reporter polypeptide is a modified variant of GFP selected from the group consisting of: EGFP, EBFP, EYFP, d2EGFP, and GFPuv.

* * * * *

UNITED STATES PATENT AND TRADEMARK OFFICE
CERTIFICATE OF CORRECTION

PATENT NO.   : 6,689,936 B1                                      Page 1 of 1
DATED        : February 10, 2004
INVENTOR(S)  : Toshio Nishiyama et al.

It is certified that error appears in the above-identified patent and that said Letters Patent is hereby corrected as shown below:

Title page,
Item [56], References Cited, OTHER PUBLICATIONS, "Mohan J." reference, after "abstract" replace "605" with -- 606 --
"Chalfie et al." reference, replace "804" with -- 805 --.

Column 59,
Line 43, after "comprising" delete "a"

Column 60,
Line 21, after "group" delete ","
Claims 10, 12, 13 and 14, replace "claim 7" with -- claim 11 --

Signed and Sealed this

Eighth Day of June, 2004

JON W. DUDAS
*Acting Director of the United States Patent and Trademark Office*

SEQUENCE LISTING

<160> NUMBER OF SEQ ID NOS: 7

<210> SEQ ID NO 1
<211> LENGTH: 5069
<212> TYPE: DNA
<213> ORGANISM: Homo sapiens

<400> SEQUENCE: 1

```
tagttattac tagcgctacc ggactcagat ctcgagctca agcttcccga ggtcctgaag      60
gaagagagta aagccatgtc tgctgttttc tagaggctgc tactgtcccc tttactgccc     120
tgaagattca gcctgcggaa gacaggggt tgccccagtg gaattcccca gccttgccta      180
gcagagccca ttccttccgc ccccagatga agcagggaga ggaagctgag tcaaagaagg    240
ctgtcaggga gggaaaaaga ggacagagcc tggagtgtgg ggagggggttt ggggaggata   300 tctgacctgg gagggggtgt tgcaaaaggc caaggatggg ccagggggat cattagtttc    360
agaaagaagt ctcagggagt cttccatcac tttcccttgg ctgaccactg gaggctttca    420
```

```
gaccaaggga tgggggatcc ctccagcttc atcccctcc ctccctttca tacagttccc    480
acaagctctg cagtttgcaa acccctaccc ctccctgag ggcctgcggt ttcctgcggg    540
tctggggtct tgcctgactt ggcagtggag actgcgggca gtggagagag gaggaggtgg   600
tgtaagccct ttctcatgct ggtgctgcca cacacacaca cacacacaca cacacacaca   660
cacacacaca ccctgacccc tgagtcagca cttgcctgtc aaggagggt ggggtcacag    720 gagcgcctcc ttaaagcccc cacaacagca gctgcagtca gacacctctg ccctcaccgg   780
taccgcgggc ccgggatcca agatctcggt actcgaggaa ctaaaaaacc agaaagttaa   840
ctggtaagtt tagtcttttt gtcttttatt tcaggtcccg gatccggtgg tggtgcaaat   900
caaagaactg ctcctcagtg gatgttgcct ttacttctag gcctgtacgg aagtgttact   960
tctgctctaa aagctgcgga attgtacccg cggccgcaat tcccggtcgc caccatggtg  1020
agcaagggcg aggagctgtt caccggggtg gtgcccatcc tggtcgagct ggacggcgac  1080
gtaaacggcc acaagttcag cgtgtccggc gagggcgagg gcgatgccac ctacggcaag  1140
ctgaccctga agttcatctg caccaccggc aagctgcccg tgcctggcc caccctcgtg   1200 accaccctga cctacggcgt gcagtgcttc agccgctacc ccgaccacat gaagcagcac  1260
gacttcttca gtccgccat gcccgaaggc tacgtccagg agcgcaccat cttcttcaag   1320
gacgacggca actacaagac ccgcgccgag gtgaagttcg agggcgacac cctggtgaac  1380
cgcatcgagc tgaagggcat cgacttcaag gaggacggca acatcctggg cacaagctg   1440 gagtacaact acaacagcca caacgtctat atcatggccg acaagcagaa gaacggcatc  1500
aaggtgaact tcaagatccg ccacaacatc gaggacggca gcgtgcagct cgccgaccac  1560
taccagcaga acacccccat cggcgacggc cccgtgctgc tgcccgacaa ccactacctg  1620
agcacccagt ccgccctgag caagaccccc aacgagaagc gcgatcacat ggtcctgctg  1680
gagttcgtga ccgccgccgg gatcactctc ggcatggacg agctgtacaa gtaaagcggc  1740
cgcgactcta gatcataatc agccatacca catttgtaga ggttttactt gctttaaaaa  1800
acctcccaca cctcccccctg aacctgaaac ataaaatgaa tgcaattgtt gttgttaact  1860 tgttattgc agcttataat ggttacaaat aaagcaatag catcacaaat ttcacaaata   1920
aagcattttt ttcactgcat tctagttgtg gtttgtccaa actcatcaat gtatcttaag  1980
gcgtaaattg taagcgttaa tattttgtta aaattcgcgt taaattttttg ttaaatcagc  2040 tcatttttta accaataggc cgaaatcggc aaaatccctt ataaatcaaa agaatagacc  2100
gagatagggt tgagtgttgt tccagtttgg aacaagagtc cactattaaa gaacgtggac  2160
tccaacgtca aagggcgaaa aaccgtctat cagggcgatg gcccactacg tgaaccatca  2220
ccctaatcaa gttttttggg gtcgaggtgc cgtaaagcac taaatcggaa ccctaaaggg  2280
agcccccgat ttagagcttg acggggaaag ccggcgaacg tggcgagaaa ggaagggaag  2340
aaagcgaaag gagcgggcgc tagggcgctg gcaagtgtag cggtcacgct gcgcgtaacc  2400
accacacccg ccgcgcttaa tgcgccgcta caggggcgcgt caggtggcac ttttcgggga  2460
aatgtgcgcg gaacccctat ttgtttattt ttctaaatac attcaaatat gtatccgctc  2520
atgagacaat aaccctgata aatgcttcaa taatattgaa aaaggaagag tcctgaggcg  2580
gaaagaacca gctgtggaat gtgtgtcagt tagggtgtgg aaagtcccca ggctcccag    2640 caggcagaag tatgcaaagc atgcatctca attagtcagc aaccaggtgt ggaaagtccc  2700
caggctcccc agcaggcaga agtatgcaaa gcatgcatct caattagtca gcaaccatag  2760
```

```
tcccgcccct aactccgccc atcccgcccc taactccgcc cagttccgcc cattctccgc    2820
cccatggctg actaattttt tttatttatg cagaggccga ggccgcctcg gcctctgagc    2880
tattccagaa gtagtgagga ggcttttttg gaggcctagg cttttgcaaa gatcgatcaa    2940
gagacaggat gaggatcgtt tcgcatgatt gaacaagatg gattgcacgc aggttctccg    3000
gccgcttggg tggagaggct attcggctat gactgggcac aacagacaat cggctgctct    3060
gatgccgccg tgttccggct gtcagcgcag gggcgcccgg ttcttttgt caagaccgac     3120 ctgtccggtg ccctgaatga actgcaagac gaggcagcgc ggctatcgtg gctggccacg    3180
acgggcgttc cttgcgcagc tgtgctcgac gttgtcactg aagcgggaag ggactggctg    3240
ctattgggcg aagtgccggg gcaggatctc ctgtcatctc accttgctcc tgccgagaaa    3300
gtatccatca tggctgatgc aatgcggcgg ctgcatacgc ttgatccggc tacctgccca    3360
ttcgaccacc aagcgaaaca tcgcatcgag cgagcacgta ctcggatgga agccggtctt    3420
gtcgatcagg atgatctgga cgaagagcat caggggctcg cgccagccga actgttcgcc    3480
aggctcaagg cgagcatgcc cgacggcgag gatctcgtcg tgacccatgg cgatgcctgc    3540
ttgccgaata tcatggtgga aaatggccgc ttttctggat tcatcgactg tggccggctg    3600
ggtgtggcgg accgctatca ggacatagcg ttggctaccc gtgatattgc tgaagagctt    3660
ggcggcgaat gggctgaccg cttcctcgtg ctttacggta tcgccgctcc cgattcgcag    3720
cgcatcgcct tctatcgcct tcttgacgag ttcttctgag cgggactctg gggttcgaaa    3780
tgaccgacca agcgacgccc aacctgccat cacgagattt cgattccacc gccgccttct    3840
atgaaaggtt gggcttcgga atcgttttcc gggacgccgg ctggatgatc ctccagcgcg    3900
gggatctcat gctggagttc ttcgcccacc ctaggggag gctaactgaa acacggaagg    3960
agacaatacc ggaaggaacc cgcgctatga cggcaataaa aagacagaat aaaacgcacg    4020
gtgttgggtc gtttgttcat aaacgcgggg ttcggtccca gggctggcac tctgtcgata    4080
ccccaccgag accccattgg ggccaatacg cccgcgtttc ttccttttcc ccaccccacc    4140
ccccaagttc gggtgaaggc ccagggctcg cagccaacgt cggggcggca ggccctgcca    4200
tagcctcagg ttactcatat atactttaga ttgatttaaa acttcatttt taatttaaaa    4260
ggatctaggt gaagatcctt tttgataatc tcatgaccaa aatcccttaa cgtgagtttt    4320
cgttccactg agcgtcagac cccgtagaaa agatcaaagg atcttcttga tccttttttt    4380
ttctgcgcgt aatctgctgc ttgcaaacaa aaaaaccacc gctaccagcg gtggtttgtt    4440
tgccggatca agagctacca actctttttc cgaaggtaac tggcttcagc agagcgcaga    4500
taccaaatac tgtccttcta gtgtagccgt agttaggcca ccacttcaag aactctgtag    4560
caccgcctac atacctcgct ctgctaatcc tgttaccagt ggctgctgcc agtggcgata    4620
agtcgtgtct taccgggttg gactcaagac gatagttacc ggataaggcg cagcggtcgg    4680
gctgaacggg gggttcgtgc acacagccca gcttggagcg aacgacctac accgaactga    4740
gatacctaca gcgtgagcta tgagaaagcg ccacgcttcc cgaagggaga aaggcggaca    4800
ggtatccggt aagcggcagg gtcggaacag gagagcgcac gagggagctt ccaggggga    4860 acgcctggta tctttatagt cctgtcgggt ttcgccacct ctgacttgag cgtcgatttt    4920
tgtgatgctc gtcaggggg cggagcctat ggaaaaacgc cagcaacgcg gcctttttac    4980
ggttcctggc cttttgctgg ccttttgctc acatgttctt tcctgcgtta tcccctgatt    5040
ctgtggataa ccgtattacc gccatgcat                                       5069
```

<210> SEQ ID NO 2
<211> LENGTH: 5069
<212> TYPE: DNA
<213> ORGANISM: Homo sapiens

<400> SEQUENCE: 2

| | | | | | |
|---|---|---|---|---|---|
| atgcatggcg | gtaatacggt | tatccacaga | atcagggat | aacgcaggaa | agaacatgtg | 60 |
| agcaaaaggc | cagcaaaagg | ccaggaaccg | taaaaaggcc | gcgttgctgg | cgttttttcca | 120 |
| taggctccgc | cccctgacg | agcatcacaa | aaatcgacgc | tcaagtcaga | ggtggcgaaa | 180 |
| cccgacagga | ctataaagat | accaggcgtt | tccccctgga | agctccctcg | tgcgctctcc | 240 |
| tgttccgacc | ctgccgctta | ccggatacct | gtccgccttt | ctcccttcgg | gaagcgtggc | 300 |
| gctttctcat | agctcacgct | gtaggtatct | cagttcggtg | taggtcgttc | gctccaagct | 360 |
| gggctgtgtg | cacgaacccc | ccgttcagcc | cgaccgctgc | gccttatccg | gtaactatcg | 420 |
| tcttgagtcc | aacccggtaa | gacacgactt | atcgccactg | gcagcagcca | ctggtaacag | 480 |
| gattagcaga | gcgaggtatg | taggcggtgc | tacagagttc | ttgaagtggt | ggcctaacta | 540 |
| cggctacact | agaaggacag | tatttggtat | ctgcgctctg | ctgaagccag | ttaccttcgg | 600 |
| aaaaagagtt | ggtagctctt | gatccggcaa | acaaaccacc | gctggtagcg | gtggtttttt | 660 |
| tgtttgcaag | cagcagatta | cgcgcagaaa | aaaaggatct | caagaagatc | ctttgatctt | 720 |
| ttctacgggg | tctgacgctc | agtggaacga | aaactcacgt | taagggattt | tggtcatgag | 780 |
| attatcaaaa | aggatcttca | cctagatcct | tttaaattaa | aaatgaagtt | ttaaatcaat | 840 |
| ctaaagtata | tatgagtaac | ctgaggctat | ggcagggcct | gccgccccga | cgttggctgc | 900 |
| gagccctggg | ccttcacccg | aacttggggg | gtggggtggg | gaaaggaag | aaacgcgggc | 960 |
| gtattggccc | caatggggtc | tcggtggggt | atcgacagag | tgccagccct | gggaccgaac | 1020 |
| cccgcgttta | tgaacaaacg | acccaacacc | gtgcgtttta | ttctgtcttt | ttattgccgt | 1080 |
| catagcgcgg | gttccttccg | gtattgtctc | cttccgtgtt | tcagttagcc | tcccctagg | 1140 |
| gtgggcgaag | aactccagca | tgagatcccc | gcgctggagg | atcatccagc | cggcgtcccg | 1200 |
| gaaaacgatt | ccgaagccca | acctttcata | gaaggcggcg | gtggaatcga | aatctcgtga | 1260 |
| tgcaggttg | ggcgtcgctt | ggtcggtcat | ttcgaacccc | agagtcccgc | tcagaagaac | 1320 |
| tcgtcaagaa | ggcgatagaa | ggcgatgcgc | tgcgaatcgg | gagcggcgat | accgtaaagc | 1380 |
| acgaggaagc | ggtcagccca | ttcgccgcca | agctcttcag | caatatcacg | ggtagccaac | 1440 |
| gctatgtcct | gatagcggtc | cgccacaccc | agccggccac | agtcgatgaa | tccagaaaag | 1500 |
| cggccatttt | ccaccatgat | attcggcaag | caggcatcgc | catgggtcac | gacgagatcc | 1560 |
| tcgccgtcgg | gcatgctcgc | cttgagcctg | gcgaacagtt | cggctggcgc | gagcccctga | 1620 |
| tgctcttcgt | ccagatcatc | ctgatcgaca | agaccggctt | ccatccgagt | acgtgctcgc | 1680 |
| tcgatgcgat | gtttcgcttg | gtggtcgaat | gggcaggtag | ccggatcaag | cgtatgcagc | 1740 |
| cgccgcattg | catcagccat | gatggatact | ttctcggcag | gagcaaggtg | agatgacagg | 1800 |
| agatcctgcc | ccggcacttc | gcccaatagc | agccagtccc | ttcccgcttc | agtgacaacg | 1860 |
| tcgagcacag | ctgcgcaagg | aacgcccgtc | gtggccagcc | acgatagccg | cgctgcctcg | 1920 |
| tcttgcagtt | cattcaggc | accggacagg | tcggtcttga | caaaaagaac | cgggcgcccc | 1980 |
| tgcgctgaca | gccggaacac | ggcggcatca | gagcagccga | ttgtctgttg | tgcccagtca | 2040 |
| tagccgaata | gcctctccac | ccaagcggcc | ggagaacctg | cgtgcaatcc | atcttgttca | 2100 |
| atcatgcgaa | acgatcctca | tcctgtctct | tgatcgatct | ttgcaaaagc | ctaggcctcc | 2160 |

-continued

```
aaaaaagcct cctcactact tctggaatag ctcagaggcc gaggcggcct cggcctctgc   2220
ataaataaaa aaaattagtc agccatgggg cggagaatgg gcggaactgg gcggagttag   2280
gggcgggatg ggcggagtta ggggcgggac tatggttgct gactaattga gatgcatgct   2340
ttgcatactt ctgcctgctg gggagcctgg ggactttcca cacctggttg ctgactaatt   2400
gagatgcatg ctttgcatac ttctgcctgc tggggagcct ggggactttc cacaccctaa   2460
ctgacacaca ttccacagct ggttctttcc gcctcaggac tcttcctttt tcaatattat   2520
tgaagcattt atcagggtta ttgtctcatg agcggataca tatttgaatg tatttagaaa   2580
aataaacaaa taggggttcc gcgcacattt ccccgaaaag tgccacctga cgcgccctgt   2640
agcggcgcat taagcgcggc gggtgtggtg gttacgcgca gcgtgaccgc tacacttgcc   2700
agcgccctag cgcccgctcc tttcgctttc ttcccttcct ttctcgccac gttcgccggc   2760
tttccccgtc aagctctaaa tcggggggctc cctttagggt tccgatttag tgctttacgg   2820
cacctcgacc ccaaaaaact tgattagggt gatggttcac gtagtgggcc atcgccctga   2880
tagacggttt ttcgcccttt gacgttggag tccacgttct ttaatagtgg actcttgttc   2940
caaactggaa caacactcaa ccctatctcg gtctattctt ttgatttata agggattttg   3000
ccgatttcgg cctattggtt aaaaatgagc tgatttaaac aaaaatttaa cgcgaatttt   3060
aacaaaatat taacgcttac aatttacgcc ttaagataca ttgatgagtt tggacaaacc   3120
acaactagaa tgcagtgaaa aaaatgcttt atttgtgaaa tttgtgatgc tattgcttta   3180
tttgtaacca ttataagctg caataaacaa gttaacaaca caattgcat tcattttatg   3240 tttcaggttc agggggaggt gtgggaggtt ttttaaagca agtaaaacct ctacaaatgt   3300
ggtatggctg attatgatct agagtcgcgg ccgctttact tgtacagctc gtccatgccg   3360
agagtgatcc cggcggcggt cacgaactcc agcaggacca tgtgatcgcg cttctcgttg   3420
gggtctttgc tcagggcgga ctgggtgctc aggtagtggt tgtcgggcag cagcacgggg   3480
ccgtcgccga tggggtgtt ctgctggtag tggtcggcga gctgcacgct gccgtcctcg   3540
atgttgtggc ggatcttgaa gttcaccttg atgccgttct tctgcttgtc ggccatgata   3600
tagacgttgt ggctgttgta gttgtactcc agcttgtgcc ccaggatgtt gccgtcctcc   3660
ttgaagtcga tgcccttcag ctcgatgcgt tcaccaggg tgtcgccctc gaacttcacc   3720
tcggcgcggg tcttgtagtt gccgtcgtcc ttgaagaaga tggtgcgctc ctggacgtag   3780
ccttcgggca tggcggactt gaagaagtcg tgctgcttca tgtggtcggg gtagcggctg   3840
aagcactgca cgccgtaggt cagggtggtc acgagggtgg gccagggcac gggcagcttg   3900
ccggtggtgc agatgaactt cagggtcagc ttgccgtagg tggcatcgcc ctcgccctcg   3960
ccggacacgc tgaacttgtg gccgtttacg tcgccgtcca gctcgaccag gatgggcacc   4020
accccggtga acagctcctc gcccttgctc accatggtgg cgaccgggaa ttgcggccgc   4080
gggtacaatt ccgcagcttt tagagcagaa gtaacacttc cgtacaggcc tagaagtaaa   4140
ggcaacatcc actgaggagc agttctttga tttgcaccac caccgatcc gggacctgaa   4200 ataaaagaca aaaagactaa acttaccagt taactttctg gttttttagt tcctcgagta   4260
ccgagatctt ggatcccggg cccgcggtac cggtgagggc agaggtgtct gactgcagct   4320
gctgttgtgg gggctttaag gaggcgctcc tgtgaccca ccctccttg acaggcaagt   4380 gctgactcag gggtcaggt gtgtgtgtgt gtgtgtgtgt gtgtgtgtgt gtgtgtgtgt   4440
ggcagcacca gcatgagaaa gggcttacac cacctcctcc tctctccact gcccgcagtc   4500
tccactgcca agtcaggcaa gaccccagac ccgcaggaaa ccgcaggccc tcaggggagg   4560
```

-continued

```
ggtagggttt tgcaaactgc agagcttgtg ggaactgtat gaaagggagg gaggggggatg    4620 aagctggagg gatcccccat cccttggtct gaaagcctcc agtggtcagc caagggaaag    4680
tgatggaaga ctccctgaga cttctttctg aaactaatga tcccctggc ccatccttgg     4740 cctttttgcaa cacccctcc caggtcagat atcctcccca aaccctccc cacactccag    4800 gctctgtcct ctttttccct ccctgacagc cttctttgac tcagcttcct ctccctgctt    4860
catctggggg cggaaggaat gggctctgct aggcaaggct ggggaattcc actggggcaa    4920 cccctgtct tccgcaggct gaatcttcag ggcagtaaag gggacagtag cagcctctag    4980
aaaacagcag acatggcttt actctcttcc ttcaggacct cgggaagctt gagctcgaga    5040
tctgagtccg gtagcgctag taataacta                                      5069

<210> SEQ ID NO 3
<211> LENGTH: 7383
<212> TYPE: DNA
<213> ORGANISM: Homo sapiens

<400> SEQUENCE: 3
gaattcgcct gggtgaaagt gagttccccg ttggaggcaa cagacgagga gaggatggaa      60
ggcctggccc ccaagaatga gccctgaggt tcagggagcg gctggagtga gccggccccca    120 gatctcccga ggtcctgaag aagagagta aagccatgtc tgctgttttc tagaggctgc     180
tactgtcccc tttactgccc tgaagattca gcctgcggaa gacaggggt tgccccagtg     240 gaattcccca gccttgccta gcagagccca ttccttccgc ccccagatga agcagggaga    300
ggaagctgag tcaaagaagg ctgtcaggga gggaaaaaga ggacagagcc tggagtgtgg    360 ggagggttt ggggaggata tctgacctgg gagggggtgt tgcaaaaggc caaggatggg    420
ccagggggat cattagtttc agaaagaagt ctcagggagt cttccatcac tttcccttgg    480
ctgaccactg gaggctttca gaccaaggga tgggggatcc ctccagcttc atccccctcc    540
ctccctttca tacagttccc acaagctctg cagtttgcaa aaccctaccc ctcccctgag    600
ggcctgcggt ttcctgcggg tctggggtct tgcctgactt ggcagtggag actgcgggca    660
gtggagagag gaggaggtgg tgtaagccct ttctcatgct ggtgctgcca cacacacaca    720
cacacacaca cacacacaca cacacacaca ccctgacccc tgagtcagca cttgcctgtc    780
aaggaggggt ggggtcacag gagcgcctcc ttaaagcccc cacaacagca gctgcagtca    840
gacacctctg ccctcaccct cgaggaactg aaaaaccaga aagttaactg gtaagtttag    900 tcttttttgtc ttttatttca ggtcccggat ccggtggtgg tgcaaatcaa gaactgctc    960 ctcagtggat gttgccttta cttctaggcc tgtacgaag tgttacttct gctctaaaag    1020
ctgcggaatt gtacccgcgg ccgcaattcc cggggatcga aagagcctgc taaagcaaaa    1080
aagaagtcac catgtcgttt actttgacca acaagaacgt gattttcgtt gccggtctgg    1140
gaggcattgg tctggacacc agcaaggagc tgctcaagcg cgatcccgtc gttttacaac    1200
gtcgtgactg ggaaaaccct ggcgttaccc aacttaatcg ccttgcagca catcccctt    1260 tcgccagctg gcgtaatagc gaagaggccc gcaccgatcg cccttcccaa cagttgcgca    1320
gcctgaatgg cgaatggcgc tttgcctggt tccggcacc agaagcggtg ccggaaagct    1380
ggctggagtg cgatcttcct gaggccgata ctgtcgtcgt cccctcaaac tggcagatgc    1440
acggttacga tgcgcccatc tacaccaacg taacctatcc cattacggtc aatccgccgt    1500 tgttcccac ggagaatccg acgggttgtt actcgctcac atttaatgtt gatgaaagct    1560
```

```
ggctacagga aggccagacg cgaattattt ttgatggcgt taactcggcg tttcatctgt  1620
ggtgcaacgg gcgctgggtc ggttacggcc aggacagtcg tttgccgtct gaatttgacc  1680
tgagcgcatt tttacgcgcc ggagaaaacc gcctcgcggt gatggtgctg cgttggagtg  1740
acggcagtta tctggaagat caggatatgt ggcggatgag cggcattttc cgtgacgtct  1800
cgttgctgca taaaccgact acacaaatca gcgatttcca tgttgccact cgctttaatg  1860
atgatttcag ccgcgctgta ctggaggctg aagttcagat gtgcggcgag ttgcgtgact  1920
acctacgggt aacagtttct ttatggcagg gtgaaacgca ggtcgccagc ggcaccgcgc  1980
ctttcggcgg tgaaattatc gatgagcgtg gtggttatgc cgatcgcgtc acactacgtc  2040
tgaacgtcga aaacccgaaa ctgtggagcg ccgaaatccc gaatctctat cgtgcggtgg  2100
ttgaactgca caccgccgac ggcacgctga ttgaagcaga agcctgcgat gtcggtttcc  2160
gcgaggtgcg gattgaaaat ggtctgctgc tgctgaacgg caagccgttg ctgattcgag  2220
gcgttaaccg tcacgagcat catcctctgc atggtcaggt catggatgag cagacgatgg  2280
tgcaggatat cctgctgatg aagcagaaca actttaacgc cgtgcgctgt tcgcattatc  2340
cgaaccatcc gctgtggtac acgctgtgcg accgctacgc cctgtatgtg gtggatgaag  2400
ccaatattga aacccacggc atggtgccaa tgaatcgtct gaccgatgat ccgcgctggc  2460
taccggcgat gagcgaacgc gtaacgcgaa tggtgcagcg cgatcgtaat cacccgagtg  2520
tgatcatctg gtcgctgggg aatgaatcag gccacggcgc taatcacgac gcgctgtatc  2580
gctggatcaa atctgtcgat ccttcccgcc ggtgcagta tgaaggcggc ggagccgaca  2640
ccacggccac cgatattatt tgcccgatgt acgcgcgcgt ggatgaagac cagcccttcc  2700
cggctgtgcc gaaatggtcc atcaaaaaat ggctttcgct acctggagag acgcgcccgc  2760
tgatccttg cgaatacgcc cacgcgatgg gtaacagtct ggcggttttc gctaaatact  2820
ggcaggcgtt tcgtcagtat ccccgtttac agggcggctt cgtctgggac tgggtggatc  2880
agtcgctgat aaatatgat gaaaacggca acccgtggtc ggcttacggc ggtgattttg  2940
gcgatacgcc gaacgatcgc cagttctgta tgaacgtct ggtctttgcc gaccgcacgc  3000
cgcatccagc gctgacggaa gcaaaacacc agcagcagtt tttccagttc cgtttatccg  3060
ggcaaaccat cgaagtgacc agcgaatacc tgttccgtca tagcgataac gagctcctgc  3120
actggatggt ggcgctggat ggtaagccgc tggcaagcgg tgaagtgcct ctggatgtcg  3180
ctccacaagg taaacagttg attgaactgc tgaactacc gcagccggag agcgccgggc  3240
aactctggct cacagtacgc gtagtgcaac cgaacgcgac cgcatggtca gaagccgggc  3300
acatcagcgc ctggcagcag tggcgtctgg cggaaaacct cagtgtgacg ctccccgccg  3360
cgtcccacgc catcccgcat ctgaccacca gcgaaatgga tttttgcatc gagctgggta  3420
ataagcgttg gcaatttaac cgccagtcag gcttctttc acagatgtgg attggcgata  3480
aaaaacaact gctgacgccg ctgcgcgatc agttcacccg tgcaccgctg gataacgaca  3540
ttggcgtaag tgaagcgacc cgcattgacc ctaacgcctg ggtcgaacgc tggaaggcgg  3600
cgggccatta ccaggccgaa gcagcgttgt tgcagtgcac ggcagataca cttgctgatg  3660
cggtgctgat tacgaccgct cacgcgtggc agcatcaggg gaaaacctta tttatcagcc  3720
ggaaaaccta ccggattgat ggtagtggtc aaatggcgat taccgttgat gttgaagtgg  3780
cgagcgatac accgcatccg gcgcggattg gcctgaactg ccagctggcg caggtagcag  3840
agcgggtaaa ctggctcgga ttagggccgc aagaaaacta tcccgaccgc ttactgccg  3900
cctgttttga ccgctgggat ctgccattgt cagacatgta taccccgtac gtcttcccga  3960
```

```
gcgaaaacgg tctgcgctgc gggacgcgcg aattgaatta tggcccacac cagtggcgcg    4020
gcgacttcca gttcaacatc agccgctaca gtcaacagca actgatggaa accagccatc    4080
gccatctgct gcacgcggaa gaaggcacat ggctgaatat cgacggtttc catatgggga    4140
ttggtggcga cgactcctgg agcccgtcag tatcggcgga attacagctg agcgccggtc    4200
gctaccatta ccagttggtc tggtgtcaaa aataataata accgggcagg ccatgtctgc    4260
ccgtatttcg cgtaaggaaa tccattatgt actatttaaa aaacacaaac ttttggatgt    4320
tcggtttatt ctttttcttt tactttttta tcatgggagc ctacttcccg ttttttcccga   4380 tttggctaca tgacatcaac catatcagca aaagtgatac gggtattatt tttgccgcta    4440
tttctctgtt ctcgctatta ttccaaccgc tgtttggtct gctttctgac aaactcggcc    4500
tcgactctag gcggccgcgg ggatccagac atgataagat acattgatga gtttggacaa    4560
accacaacta gaatgcagtg aaaaaaatgc tttatttgtg aaatttgtga tgctattgct    4620
ttatttgtaa ccattataag ctgcaataaa caagttaaca acaacaattg cattcatttt    4680
atgtttcagg ttcagggggga ggtgtgggag gttttttcgg atcctctaga gtcgacctgc    4740
aggcatgcaa gcttggcgta atcatggtca tagctgtttc ctgtgtgaaa ttgttatccg    4800
ctcacaattc cacacaacat acgagccgga agcataaagt gtaaagcctg gggtgcctaa    4860
tgagtgagct aactcacatt aattgcgttg cgctcactgc ccgctttcca gtcgggaaac    4920
ctgtcgtgcc agctgcatta atgaatcggc caacgcgcgg ggagaggcgg tttgcgtatt    4980
gggcgctctt ccgcttcctc gctcactgac tcgctgcgct cggtcgttcg ctgcggcga    5040 gcggtatcag ctcactcaaa ggcggtaata cggttatcca cagaatcagg ggataacgca    5100
ggaaagaaca tgtgagcaaa aggccagcaa aaggccagga accgtaaaaa ggccgcgttg    5160
ctggcgtttt tccataggct ccgcccccct gacgagcatc acaaaaatcg acgctcaagt    5220
cagaggtggc gaaacccgac aggactataa agataccagg cgtttccccc tggaagctcc    5280
ctcgtgcgct ctcctgttcc gaccctgccg cttaccggat acctgtccgc ctttctccct    5340
tcgggaagcg tggcgctttc tcatagctca cgctgtaggt atctcagttc ggtgtaggtc    5400
gttcgctcca agctgggctg tgtgcacgaa ccccccgttc agcccgaccg ctgcgcctta    5460
tccggtaact atcgtcttga gtccaacccg gtaagacacg acttatcgcc actggcagca    5520
gccactggta acaggattag cagagcgagg tatgtaggcg gtgctacaga gttcttgaag    5580
tggtggccta actacggcta cactagaagg acagtatttg gtatctgcgc tctgctgaag    5640
ccagttacct tcggaaaaag agttggtagc tcttgatccg gcaaacaaac caccgctggt    5700
agcggtggtt tttttgtttg caagcagcag attacgcgca gaaaaaaagg atctcaagaa    5760
gatcctttga tcttttctac ggggtctgac gctcagtgga acgaaaactc acgttaaggg    5820
attttggtca tgagattatc aaaaaggatc ttcacctaga tccttttaaa ttaaaaatga    5880
agttttaaat caatctaaag tatatatgag taaacttggt ctgacagtta ccaatgctta    5940
atcagtgagg cacctatctc agcgatctgt ctatttcgtt catccatagt tgcctgactc    6000
cccgtcgtgt agataactac gatacgggag ggcttaccat ctggccccag tgctgcaatg    6060
ataccgcgag acccacgctc accggctcca gatttatcag caataaacca gccagccgga    6120
agggccgagc gcagaagtgg tcctgcaact ttatccgcct ccatccagtc tattaattgt    6180
tgccgggaag ctagagtaag tagttcgcca gttaatagtt tgcgcaacgt tgttgccatt    6240
gctacaggca tcgtggtgtc acgctcgtcg tttggtatgg cttcattcag ctccggttcc    6300
```

-continued

| | |
|---|---|
| caacgatcaa ggcgagttac atgatccccc atgttgtgca aaaaagcggt tagctccttc | 6360 |
| ggtcctccga tcgttgtcag aagtaagttg gccgcagtgt tatcactcat ggttatggca | 6420 |
| gcactgcata attctcttac tgtcatgcca tccgtaagat gcttttctgt gactggtgag | 6480 |
| tactcaacca agtcattctg agaatagtgt atgcggcgac cgagttgctc ttgcccggcg | 6540 |
| tcaatacggg ataataccgc gccacatagc agaactttaa aagtgctcat cattggaaaa | 6600 |
| cgttcttcgg ggcgaaaact ctcaaggatc ttaccgctgt tgagatccag ttcgatgtaa | 6660 |
| cccactcgtg cacccaactg atcttcagca tcttttactt tcaccagcgt ttctgggtga | 6720 |
| gcaaaaacag gaaggcaaaa tgccgcaaaa aagggaataa gggcgacacg gaaatgttga | 6780 |
| atactcatac tcttcctttt tcaatattat tgaagcattt atcagggtta ttgtctcatg | 6840 |
| agcggataca tatttgaatg tatttagaaa aataaacaaa taggggttcc gcgcacattt | 6900 |
| ccccgaaaag tgccacctga cgtctaagaa accattatta tcatgacatt aacctataaa | 6960 |
| aataggcgta tcacgaggcc ctttcgtctc gcgcgtttcg gtgatgacgg tgaaaacctc | 7020 |
| tgacacatgc agctcccgga gacggtcaca gcttgtctgt aagcggatgc cgggagcaga | 7080 |
| caagcccgtc agggcgcgtc agcgggtgtt ggcgggtgtc ggggctggct taactatgcg | 7140 |
| gcatcagagc agattgtact gagagtgcac catatgcggt gtgaaatacc gcacagatgc | 7200 |
| gtaaggagaa aataccgcat caggcgccat tcgccattca ggctgcgcaa ctgttgggaa | 7260 |
| gggcgatcgg tgcgggcctc ttcgctatta cgccagctgg cgaaaggggg atgtgctgca | 7320 |
| aggcgattaa gttgggtaac gccagggttt tcccagtcac gacgttgtaa aacgacggcc | 7380 |
| agt | 7383 |

<210> SEQ ID NO 4
<211> LENGTH: 7383
<212> TYPE: DNA
<213> ORGANISM: Homo sapiens

<400> SEQUENCE: 4

| | |
|---|---|
| actggccgtc gttttacaac gtcgtgactg ggaaaaccct ggcgttaccc aacttaatcg | 60 |
| ccttgcagca catcccccett tcgccagctg gcgtaatagc gaagaggccc gcaccgatcg | 120 |
| cccttcccaa cagttgcgca gcctgaatgg cgaatggcgc ctgatgcggt attttctcct | 180 |
| tacgcatctg tgcggtattt cacaccgcat atggtgcact ctcagtacaa tctgctctga | 240 |
| tgccgcatag ttaagccagc cccgacaccc gccaacaccc gctgacgcgc cctgacgggc | 300 |
| ttgtctgctc ccggcatccg cttacagaca agctgtgacc gtctccggga gctgcatgtg | 360 |
| tcagaggttt tcaccgtcat caccgaaacg cgcgagacga aagggcctcg tgatacgcct | 420 |
| atttttatag gttaatgtca tgataataat ggtttcttag acgtcaggtg gcacttttcg | 480 |
| gggaaatgtg cgcggaaccc ctatttgttt attttctaa atacattcaa atatgtatcc | 540 |
| gctcatgaga caataaccct gataaatgct tcaataatat tgaaaaagga agagtatgag | 600 |
| tattcaacat ttccgtgtcg cccttattcc cttttttgcg gcattttgcc ttcctgtttt | 660 |
| tgctcaccca gaaacgctgg tgaaagtaaa agatgctgaa gatcagttgg gtgcacgagt | 720 |
| gggttacatc gaactggatc tcaacagcgg taagatcctt gagagttttc gccccgaaga | 780 |
| acgttttcca atgatgagca cttttaaagt tctgctatgt ggcgcggtat tatcccgtat | 840 |
| tgacgccggg caagagcaac tcggtcgccg catacactat tctcagaatg acttggttga | 900 |
| gtactcacca gtcacagaaa agcatcttac ggatggcatg acagtaagag aattatgcag | 960 |
| tgctgccata accatgagtg ataacactgc ggccaactta cttctgacaa cgatcggagg | 1020 |

```
accgaaggag ctaaccgctt ttttgcacaa catgggggat catgtaactc gccttgatcg   1080
ttgggaaccg gagctgaatg aagccatacc aaacgacgag cgtgacacca cgatgcctgt   1140
agcaatggca acaacgttgc gcaaactatt aactggcgaa ctacttactc tagcttcccg   1200
gcaacaatta atagactgga tggaggcgga taaagttgca ggaccacttc tgcgctcggc   1260
ccttccggct ggctggttta ttgctgataa atctggagcc ggtgagcgtg gtctcgcgg    1320 tatcattgca gcactgggc cagatggtaa gccctcccgt atcgtagtta tctacacgac    1380
ggggagtcag gcaactatgg atgaacgaaa tagacagatc gctgagatag gtgcctcact   1440
gattaagcat tggtaactgt cagaccaagt ttactcatat atactttaga ttgatttaaa   1500
acttcatttt taatttaaaa ggatctaggt gaagatcctt tttgataatc tcatgaccaa   1560
aatcccttaa cgtgagtttt cgttccactg agcgtcagac cccgtagaaa agatcaaagg   1620
atcttcttga tccttttt ttctgcgcgt aatctgctgc ttgcaaacaa aaaaaccacc     1680
gctaccagcg gtggtttgtt tgccggatca agagctacca actcttttc cgaaggtaac    1740 tggcttcagc agagcgcaga taccaaatac tgtccttcta gtgtagccgt agttaggcca   1800
ccacttcaag aactctgtag caccgcctac atacctcgct ctgctaatcc tgttaccagt   1860
ggctgctgcc agtggcgata gtcgtgtct taccggttg gactcaagac gatagttacc     1920
ggataaggcg cagcggtcgg gctgaacggg gggttcgtgc acacagccca gcttggagcg   1980
aacgacctac accgaactga gatacctaca gcgtgagcta tgagaaagcg ccacgcttcc   2040
cgaagggaga aggcggaca ggtatccggt aagcggcagg gtcggaacag gagagcgcac    2100
gagggagctt ccaggggaa acgcctggta tctttatagt cctgtcgggt ttcgccacct    2160
ctgacttgag cgtcgatttt tgtgatgctc gtcaggggg cggagcctat ggaaaaacgc    2220
cagcaacgcg gcctttttac ggttcctggc cttttgctgg ccttttgctc acatgttctt   2280
tcctgcgtta tcccctgatt ctgtggataa ccgtattacc gcctttgagt gagctgatac   2340
cgctcgccgc agccgaacga ccgagcgcag cgagtcagtg agcgaggaag cggaagagcg   2400
cccaatacgc aaaccgcctc tccccgcgcg ttggccgatt cattaatgca gctggcacga   2460
caggtttccc gactggaaag cgggcagtga gcgcaacgca attaatgtga gttagctcac   2520
tcattaggca ccccaggctt tacactttat gcttccggct cgtatgttgt gtggaattgt   2580
gagcggataa caatttcaca caggaaacag ctatgaccat gattacgcca agcttgcatg   2640
cctgcaggtc gactctagag gatccgaaaa aacctcccac acctcccct gaacctgaaa    2700 cataaaatga atgcaattgt tgttgttaac ttgtttattg cagcttataa tggttacaaa   2760
taaagcaata gcatcacaaa tttcacaaat aaagcatttt tttcactgca ttctagttgt   2820
ggtttgtcca aactcatcaa tgtatcttat catgtctgga tccccgcggc cgcctagagt   2880
cgaggccgag tttgtcagaa agcagaccaa acagcggttg gaataatagc gagaacagag   2940
aaatagcggc aaaaataata cccgtatcac ttttgctgat atggttgatg tcatgtagcc   3000
aaatcgggaa aaacgggaag taggctccca tgataaaaaa gtaaagaaa agaataaac     3060 cgaacatcca aaagtttgtg ttttttaaat agtacataat ggatttcctt acgcgaaata   3120
cgggcagaca tggcctgccc ggttattatt attttgaca ccagaccaac tggtaatggt    3180
agcgaccggc gctcagctgt aattccgccg atactgacgg gctccaggag tcgtcgccac   3240
caatccccat atgaaaccg tcgatattca gccatgtgcc ttcttccgcg tgcagcagat    3300
ggcgatggct ggtttccatc agttgctgtt gactgtagcg gctgatgttg aactggaagt   3360
```

-continued

```
cgccgcgcca ctggtgtggg ccataattca attcgcgcgt cccgcagcgc agaccgtttt    3420
cgctcgggaa gacgtacggg gtatacatgt ctgacaatgg cagatcccag cggtcaaaac    3480
aggcggcagt aaggcggtcg ggatagtttt cttgcggccc taatccgagc cagtttaccc    3540
gctctgctac ctgcgccagc tggcagttca ggccaatccg cgccggatgc ggtgtatcgc    3600
tcgccacttc aacatcaacg gtaatcgcca tttgaccact accatcaatc cggtaggttt    3660
tccggctgat aaataaggtt ttcccctgat gctgccacgc gtgagcggtc gtaatcagca    3720
ccgcatcagc aagtgtatct gccgtgcact gcaacaacgc tgcttcggcc tggtaatggc    3780
ccgccgcctt ccagcgttcg acccaggcgt tagggtcaat gcgggtcgct tcacttacgc    3840
caatgtcgtt atccagcggt gcacgggtga actgatcgcg cagcggcgtc agcagttgtt    3900
ttttatcgcc aatccacatc tgtgaaagaa agcctgactg gcggttaaat tgccaacgct    3960
tattacccag ctcgatgcaa aaatccattt cgctggtggt cagatgcggg atggcgtggg    4020
acgcggcggg gagcgtcaca ctgaggtttt ccgccagacg ccactgctgc caggcgctga    4080
tgtgcccggc ttctgaccat gcggtcgcgt tcggttgcac tacgcgtact gtgagccaga    4140
gttgcccggc gctctccggc tgcggtagtt caggcagttc aatcaactgt ttaccttgtg    4200
gagcgacatc cagaggcact tcaccgcttg ccagcggctt accatccagc gccaccatcc    4260
agtgcaggag ctcgttatcg ctatgacgga acaggtattc gctggtcact tcgatggttt    4320
gcccggataa acggaactgg aaaaactgct gctggtgttt tgcttccgtc agcgctggat    4380
gcggcgtgcg gtcggcaaag accagaccgt tcatacagaa ctggcgatcg ttcggcgtat    4440
cgccaaaatc accgccgtaa gccgaccacg ggttgccgtt ttcatcatat ttaatcagcg    4500
actgatccac ccagtcccag acgaagccgc cctgtaaacg gggatactga cgaaacgcct    4560
gccagtattt agcgaaaccg ccaagactgt tacccatcgc gtgggcgtat tcgcaaagga    4620
tcagcgggcg cgtctctcca ggtagcgaaa gccattttt gatggaccat ttcggcacag    4680
ccgggaaggg ctggtcttca tccacgcgcg cgtacatcgg gcaaataata tcggtggccg    4740
tggtgtcggc tccgccgcct tcatactgca ccgggcggga aggatcgaca gatttgatcc    4800
agcgatacag cgcgtcgtga ttagcgccgt ggcctgattc attccccagc gaccagatga    4860
tcacactcgg gtgattacga tcgcgctgca ccattcgcgt tacgcgttcg ctcatcgccg    4920
gtagccagcg cggatcatcg gtcagacgat tcattggcac catgccgtgg gtttcaatat    4980
tggcttcatc caccacatac aggccgtagc ggtcgcacag cgtgtaccac agcggatggt    5040
tcggataatg cgaacagcgc acggcgttaa agttgttctg cttcatcagc aggatatcct    5100
gcaccatcgt ctgctcatcc atgacctgac catgcagagg atgatgctcg tgacggttaa    5160
cgcctcgaat cagcaacggc ttgccgttca gcagcagcag accattttca atccgcacct    5220
cgcggaaacc gacatcgcag gcttctgctt caatcagcgt gccgtcggcg gtgtgcagtt    5280
caaccaccgc acgatagaga ttcgggattt cggcgctcca cagtttcggg ttttcgacgt    5340
tcagacgtag tgtgacgcga tcggcataac caccacgctc atcgataatt tcaccgccga    5400
aaggcgcggt gccgctggcg acctgcgttt caccctgcca taaagaaact gttacccgta    5460
ggtagtcacg caactcgccg cacatctgaa cttcagcctc cagtacagcg cggctgaaat    5520
catcattaaa gcgagtggca acatggaaat cgctgatttg tgtagtcggt ttatgcagca    5580
acgagacgtc acggaaaatg ccgctcatcc gccacatatc ctgatcttcc agataactgc    5640
cgtcactcca acgcagcacc atcaccgcga ggcggttttc tccggcgcgt aaaaatgcgc    5700
tcaggtcaaa ttcagacggc aaacgactgt cctggccgta accgacccag cgccgttgc    5760
```

```
accacagatg aaacgccgag ttaacgccat caaaaataat tcgcgtctgg ccttcctgta      5820
gccagctttc atcaacatta aatgtgagcg agtaacaacc cgtcggattc tccgtgggaa      5880
caaacggcgg attgaccgta atgggatagg ttacgttggt gtagatgggc gcatcgtaac      5940
cgtgcatctg ccagtttgag gggacgacga cagtatcggc ctcaggaaga tcgcactcca      6000
gccagctttc cggcaccgct tctggtgccg gaaaccagge aaagcgccat cgccattca       6060 ggctgcgcaa ctgttgggaa gggcgatcgg tgcgggcctc ttcgctatta cgccagctgg      6120 cgaaggggg atgtgctgca aggcgattaa gttgggtaac gccagggttt tcccagtcac       6180
gacgttgtaa aacgacggga tcgcgcttga gcagctcctt gctggtgtcc agaccaatgc      6240
ctcccagacc ggcaacgaaa tcacgttct  tgttggtcaa agtaaacgac atggtgactt      6300 ctttttgct  ttagcaggct ctttcgatcc ccgggaattg cggccgcggg tacaattccg      6360
cagcttttag agcagaagta acacttccgt acaggcctag aagtaaaggc aacatccact      6420
gaggagcagt tctttgattt gcaccaccac cggatccggg acctgaaata aagacaaaa      6480 agactaaact taccagttaa ctttctggtt tttcagttcc tcgagggtga gggcagaggt      6540
gtctgactgc agctgctgtt gtgggggctt taaggaggcg ctcctgtgac cccaccctc      6600 cttgacaggc aagtgctgac tcaggggtca gggtgtgtgt gtgtgtgtgt gtgtgtgtgt      6660
gtgtgtgtgt gtgtggcagc accagcatga gaaagggctt acaccacctc ctcctctctc      6720
cactgcccgc agtctccact gccaagtcag gcaagacccc agaccgcag  gaaaccgcag      6780 gccctcaggg gaggggtagg gttttgcaaa ctgcagagct tgtgggaact gtatgaaagg      6840
gagggagggg gatgaagctg gagggatccc ccatcccttg gtctgaaagc ctccagtggt      6900
cagccaaggg aaagtgatgg aagactccct gagacttctt tctgaaacta atgatccccc      6960
tggcccatcc ttggcctttt gcaacacccc ctcccaggtc agatatcctc ccaaaccccc      7020
tccccacact ccaggctctg tcctcttttt ccctccctga cagccttctt tgactcagct      7080
tcctctccct gcttcatctg ggggcggaag gaatgggctc tgctaggcaa ggctggggaa      7140
ttccactggg gcaaccccct gtcttccgca ggctgaatct tcagggcagt aaaggggaca      7200
gtagcagcct ctagaaaaca gcagacatgg ctttactctc ttccttcagg acctcgggag      7260
atctggggcc ggctcactcc agccgctccc tgaacctcag ggctcattct tgggggccag      7320
gccttccatc ctctcctcgt ctgttgcctc caacggggaa ctcactttca cccaggcgaa      7380
ttc                                                                     7383
```

<210> SEQ ID NO 5
<211> LENGTH: 30
<212> TYPE: DNA
<213> ORGANISM: Artificial Sequence
<220> FEATURE:
<223> OTHER INFORMATION: probe

<400> SEQUENCE: 5
ccgttctggg ccaccaagac agtcgtctcc                                          30

<210> SEQ ID NO 6
<211> LENGTH: 30
<212> TYPE: DNA
<213> ORGANISM: Artificial Sequence
<220> FEATURE:
<223> OTHER INFORMATION: probe

<400> SEQUENCE: 6

```
                                        -continued
tgaccgcccc gatatccaaa caagcctgtt                                              30

<210> SEQ ID NO 7
<211> LENGTH: 30
<212> TYPE: DNA
<213> ORGANISM: Artificial Sequence
<220> FEATURE:
<223> OTHER INFORMATION: probe

<400> SEQUENCE: 7
tccgacagcc agccgtaatc gcattggtca                                              30
```